United States Patent
Tanaka et al.

[11] Patent Number: 5,942,641
[45] Date of Patent: Aug. 24, 1999

[54] FLUORENONE DERIVATIVES, PROCESS FOR PREPARING THE SAME AND CENTRAL OR PERIPHERAL NERVE DEGENERATION REPAIR AND PROTECTIVE AGENT

[75] Inventors: Tatsuyoshi Tanaka; Yohji Sakurai; Nobutaka Fujisawa; Osamu Hongoh; Takao Nishi, all of Itano-gun, Japan

[73] Assignee: Otsuka Pharmaceutical Co., Ltd., Tokyo, Japan

[21] Appl. No.: 08/381,865

[22] PCT Filed: Jun. 15, 1994

[86] PCT No.: PCT/JP94/00966

§ 371 Date: Feb. 7, 1995

§ 102(e) Date: Feb. 7, 1995

[87] PCT Pub. No.: WO95/00468

PCT Pub. Date: Jan. 5, 1995

[30] Foreign Application Priority Data

Jun. 18, 1993 [JP] Japan ..................... 5-147740

[51] Int. Cl.⁶ ............ C07C 69/00; C07C 49/215; A61K 31/12
[52] U.S. Cl. ............ 560/139; 568/326; 514/680
[58] Field of Search .............. 568/326; 514/680; 560/139

[56] References Cited

U.S. PATENT DOCUMENTS

| | | | |
|---|---|---|---|
| 3,622,580 | 11/1971 | Hromtka | 260/268 |
| 3,639,624 | 2/1972 | Shen et al. | 424/317 |
| 3,903,145 | 9/1975 | Levine et al. | 260/515 R |
| 3,929,862 | 12/1975 | Morozowich | 260/468 D |
| 3,959,319 | 5/1976 | Morozowich | 260/390 |
| 3,987,067 | 10/1976 | Morozowich | 260/395 |
| 4,096,267 | 6/1978 | Cragoe, Jr. et al. | 424/267 |
| 4,447,420 | 5/1984 | Traxler | 424/210 |
| 4,683,241 | 7/1987 | Miyano et al. | 514/512 |
| 4,801,610 | 1/1989 | Miyano et al. | 514/512 |
| 4,996,230 | 2/1991 | Gapinski | 514/454 |

FOREIGN PATENT DOCUMENTS

| | | |
|---|---|---|
| 0267024 B1 | 5/1988 | European Pat. Off. |
| 0325035 | 7/1989 | European Pat. Off. |
| 0382213 | 8/1990 | European Pat. Off. |
| 0455219 A1 | 6/1991 | European Pat. Off. |
| 0469844 A1 | 2/1992 | European Pat. Off. |
| 2348534 | 4/1974 | Germany |
| 2812542 | 3/1978 | Germany |
| 47-45335 | 11/1972 | Japan |
| 48-92357 | 11/1973 | Japan |
| 49-84432 | 8/1974 | Japan |
| 49-93352 | 9/1974 | Japan |
| 57-176968 | 10/1982 | Japan |
| 58-178956 | 10/1983 | Japan |
| 60-104027 | 6/1985 | Japan |
| 60-215080 | 10/1985 | Japan |
| 63-220251 | 9/1988 | Japan |
| 1-200362 | 8/1989 | Japan |
| 1365124 | 10/1974 | United Kingdom |

OTHER PUBLICATIONS

Chemical Abstract 57:12395f, Jul. 1962 Notes, pp. 2643–2644.

Chemical Abstract, vol. 58:6712B, 1963, Speake, "Giberillic acid". XIX. The Degradation . . . Studies on Uronic Acid Materials Part VI, pp. 6–15, (58:6712b).

Chemical Abstracts vol. 100, No. 11, issued Mar. 12, 1984, Litvinoa—"3,6–Disubstituted fluoren–9–ones . . . " (100(11):853612).

Chemical Abstract, vol. 83, No. 23, issued 1975, Thomas et al.—"Synthesis of Oxygen Heterocyclics . . . " (83(23):193012a).

Science, vol. 214, No. 4520, issued Oct. 1981, Roisen et al.—"Ganglioside stimulation of axonal . . . ".

Science, vol. 235, issued Jan. 1987, Kromer—"Nerve Growth Factor Treatment After Brain Injury . . . ".

Chemical Abstract 63:17859a, Zeitxchrift fur Naturforschung, pp. 617–624, 1965.

Chemical Abstract 71(25):124137k, J. Chemical Society (C), 1969, pp. 2138–2143.

Chemical Abstract 87(1):5572u, Communications Synthesis, pp. 186–189, 1977.

(List continued on next page.)

Primary Examiner—Gary Geist
Assistant Examiner—Rosalynd Keys
Attorney, Agent, or Firm—Sughrue, Mion, Zinn, Macpeak & Seas, PLLC

[57] ABSTRACT

The present invention provides a novel fluorenone derivatives represented by the formula:

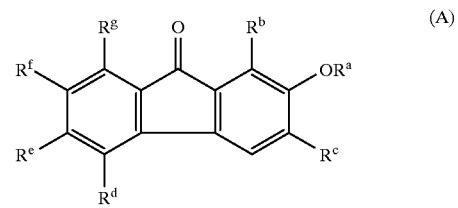

(A)

wherein $R^a$–$R^g$ are defined in the specification, and a method for repairing and protecting central or peripheral nerve degeneration comprising use of a fluorenone derivative represented by the formula:

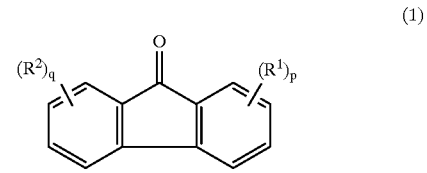

(1)

wherein $R^1$, $R^2$ p and q are as defined in the specification as an active component.

33 Claims, No Drawings

OTHER PUBLICATIONS

Chem. Abstract 93(21): 204222d, Jour. of the Amer. Chem. Society/102:10/May 7, 1980, pp. 3534–3539.
Chemical Abstract 57:2157h, Barnes and Faessinger, vol. 26, Nov. 1961, pp. 4544–4548.
Chemical Abstract 53:1278g, Investigations of Reduced Cyclic Bases, Part VI., etc., pp. 2692–2701, 1958.
Chemical Abstract 55:488b, Cross and Melvin: et c., pp. 3038–3041, 1960.
Chemical Abstract 114(19)185176a, J. Chemical Society, Perkin Trans., 1, 1991, pp. 385–393.
Chemical Abstract 79(13): 78450x, L. Horner and D.W. Baston, etc., pp. 910–935, 1973.
Chemical Abstract 116(5):41184v, J. Org. Chem. 1992, 57, pp. 424–427.
Chemical Abstract 114(17):163688s, J. Org. Chem., vol. 56, No. 5, 1991, pp. 1682–1685.
Chemical Abstract 113 (11):94748b, J. Indian Chem. Soc., vol. 66, Nov. 1989, pp. 834–837.
Chemical Abstract 110(5):38805u, Indian Journal of Chemistry, vol. 27B, Mar. 1988, pp. 250–252.
Chemical Abstract 108(25):221476k, J. Chem. Society Perkin Trans., 1, 1987, pp. 2553–2563.
Chemical Abstract 103(19):157294s, On the Chemistry of the Indian Orchidaceae Plants–II,1985,pp. 2765–2767.
Chemical Abstract 103(13):102029d, J. Indian Chem. Society, vol. LXI, Nov., Dec. 1984, pp.1010–1012.
Chemical Abstract 67(19):90567a, T.L. Fletcher et al., vol. 10, etc. pp. 936–941, Sep. 1967.
Chemical Abstract 87(11):94716v, Tetrahedron Letters No. 10, 1977, pp. 854–859.
Chemical Abstract 100(11):79474x, Molecular Pharmacology, 24, pp. 521–531, 1984.
Chemical Abstract, vol. 82, No. 19, issued May 12, 1975, Thomas et al.–13 "Bromination . . . " 82(19):12150y.
Chemical Abstract 94(7):47004k, The Chemical Society of Japan, vol. 53, No. 8, 1980, pp. 2334–2339.
Chemical Abstract 111(21)186953b, Khim.–Farm. Zh., 1989, 23(6), 702–4.
Chemical Abstract 109(5):37593r, Khim–Farm. Zh., 21(10), 1203–6, 1987.
Chemical Abstract 98(9):71618s, Khim.–Farm. Zh, 16(9), 1058–9, 1982.
Chemical Abstract 113(15):131696f, Journal f. prakt. Chemie, Band 332, Heft 1, 1990, pp. 5–14.
Chemical Abstract 53:3168b, Studies on the Fluorene Derivatives, XII, pp. 610–615, 1958.
Chemical Abstract 103(5):124121e, JP–A–60–71635, Apr. 23, 1985.
Chemical Abstract 100(17):139054x, Khim. Geterotsikl. Soedin, (II), 1537–9, 1983.
Chemical Abstract 82(5):25667d, Journal of Medical Chemistry, 1974, vol. 17, No. 8, pp. 882–887.
Chemical Abstract 112(25):234935s, The Chemical Society of Japan, 1989, (12), pp. 2052–2058.
Chemical Abstract 58:6736g, B. Eistert and E.A. Hackman Bd., 657, pp. 120–131, 1962.
CA 109(25):221959r, Khim–Farm. Zh., 22(8), 977–9, 1988.
CA 55:27235b, Suzuki, Weisburger and Weisburger, J. Org. Chem. vol. 26, pp. 2236–2239, 1961.
Boyki et al., $^{17}O$ NMR Spectroscopic Study of Substituted 9–Fluorens, Magentic Resonance in Chemistry, vol. 29, pp. 152–155, 1991.
Russian Document, TOM 36, 1991, pp. 82–85.
Russian Document, CA 96(11):85199b, pp. 2456–2457, 1981.
Burke et al., *New Synthetic Pathways to Tilorone Hydrochlorid*, Synthetic Communications, vol. 6(5), pp. 371–376, 1976.
Paolo Da Re et al., *Structure–activity relationships in centrally stimulating xanthone derivatives . . .* , Chimie Therapeutique, Jan.–Feb. 1973, No. 1, pp. 49–53.
Eistert et al., *Versuche mti „Indanocyclon*, Eistert and El–Chahawi, Chem. Ber. 103, 173–182, 1970.
Thomas et al., "Synthesis of . . . and 2–hydroxyfluorenone", J. Indian Chem. Soc. 52 (7), p. 612. 1975.
Gelin et al., "Synthesis . . . via 4–acetyl–. . . –2,3–dihydrofurans", Synthesis (3), p. 187, 1977.
Barnes et al., "Synthesis Related . . . Substituted Fluorenes", J. Org. Chem. 26, p. 4547, 1961.
Fuson et al., "Conversion of 2–duroylresocinol . . . Fluorenone Derivative", J. Org. Chem. 27, p. 2643, 1962.
Horner et al., "Quinones . . . Fluorene and Fluorenone", Justus Liebigs Ann. Chem. (5–6), p. 915, 1973.
Wang et al., "Remote Directed . . . Natural Fluorenone Dengibsin", J. Org. Chem. 57(2), p. 425, 1992.
Talaptra et al., "Revised Structures . . . Chelated Methoxyls", Indian J. of Chem. 27B, p. 250, 1988.
Sargent et al., "The Structure and Synth . . . Dengibsinin", J. Chem. Soc. Perkin Trans. 1, p. 2554, 1987.
Talaptra et al., "On the Chemistry . . . Dendrobium Gibsonii Lindl", Tetrahedron 41(13), p. 4765, 1985.
Litvinova et al., "3,6–Disubstituted Fluoren–9–ones . . . Activity", Khim.–Farm. Zh. 17(10), abstract, 1983.

FLUORENONE DERIVATIVES, PROCESS FOR PREPARING THE SAME AND CENTRAL OR PERIPHERAL NERVE DEGENERATION REPAIR AND PROTECTIVE AGENT

TECHNICAL FIELD

The present invention relates to a fluorenone derivative, a process for preparing the same and a central or peripheral nerve degeneration repair or protective agent.

BACKGROUND ART

At present, it is suggested that senile demantia represented by Alzheimer's disease causes serious change in central cholinergic nervous system, which results in deterioration of function thereof [Perry, E. K. and Perry, R. H. "Biochemistry of Dementia", page 135 (1980), John Wiley & Sons.,].

Accordingly, a compound having repair capacity (e.g. survival effect and neulite stretching effect) and protective action of nerve cells can be effectively used as a remedy or a preventive for senile demantia represented by Alzheimer's disease, Down's syndrome, Huntington's chorea, intellectual/learning disturbance (e.g. amnesia, memory disorder, etc.), and aftereffect and neuropathy caused by deterioration of acetylcholinergic nervous system function due to head injury, cerebral operation, drug intoxication, circulatory disorder, cerebral metabolic disorder, encephalitis, etc. [J. W. Geddes et al., Science, 230, 1179–1181 (1985)].

Heretofore, NGF (nerve growth factor), GM1 (ganglioside) and the like have merely been known as the compound having repair capacity for nerve cells degeneration as described above. NGF is described, for example, in Neuroscience [Hefti, F. et al., 14, 55–68 (1985)], Journal of Neuroscience [Frantz Hefti, 6, 2155–2162 (1986)], Proc. Natl. Acad. Sci. USA, L. R. Williams et al., 83, 9231–9235 (1986)], Science [L. E. Kromer, 235, 214–216 (1986)] and the like. In addition, GM1 is described, for example, in Science [Fred J. Roisen et al., 214, 577–578 (1981)], Brain Res. [M. V. Sofroniew et al. 398, 393–396 (1986)], Brain Res. [M. Gradkowska et al., 375, 417–422 (1986)] and the like.

DISCLOSURE OF INVENTION

A fluorenone derivative of the present invention is represented by the following formulas (A) to (D).

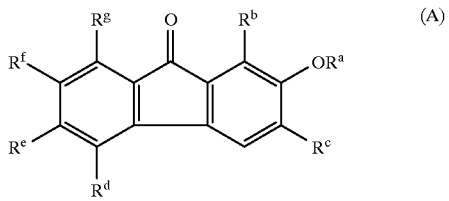

[wherein $R^a$ is a hydrogen atom, a lower alkenyl group or an acetyl group;

$R^b$ and $R^c$ are the same or different and are a hydrogen atom, a lower alkenyl group, a lower alkyl group, a halogen atom, a lower alkoxy group, a lower alkylthio group, a lower alkenyloxy group, a group of the formula:

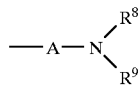

(wherein $R^8$ and $R^9$ are the same or different and indicate a hydrogen atom, a lower alkyl group, a lower alkoxycarbonyl-substituted lower alkyl group, a pyrimidinyl group or pyrazinyl group, and $R^8$ and $R^9$ may bond together with the nitrogen atom to which they are attached to form a 5- or 6-membered saturated heterocycle through a nitrogen or oxygen atom or not (i.e., having a nitrogen or oxygen atom or not as other hetero atom), the heterocycle optionally containing a substituent selected from the group consisting of a lower alkyl group and a lower alkoxycarbonyl group; and A is a lower alkylene group), an imidazolyl-substituted lower alkyl group, a lower alkoxy-substituted lower alkyl group, a hydroxyl group-substituted lower alkoxy-lower alkoxy-substituted lower alkyl group or a lower trialkyl-substituted ammonium-substituted lower alkyl group;

$R^d$, $R^e$, $R^f$ and $R^g$ are the same or different and are; a hydrogen atom, a lower alkenyl group, a lower alkyl group, a halogen atom, a lower alkoxy group, a lower alkenyloxy group, a group of the formula:

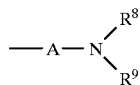

(wherein $R^8$ and $R^9$ are as defined above), an imidazolyl-substituted lower alkyl group, a lower alkoxy-substituted lower alkyl group, a pyridylthio-substituted lower alkyl group, a phenylthio-substituted lower alkyl group optionally containing a lower alkoxy group as a substituent on a phenyl ring, a benzimidazolylthio-substituted lower alkyl group, an imidazolylthio-substituted lower alkyl group, a lower alkanoyl group, a cycloalkylthio-substituted lower alkyl group, a cyano-substituted lower alkyl group or a lower trialkyl-substituted ammonium-substituted lower alkyl group;

(1) $R^c$ and $R^g$ must not be methyl groups when $R^a$, $R^b$, $R^d$, $R^e$ and $R^f$ are hydrogen atoms, (2) $R^f$ must not be a methyl group when $R^a$, $R^b$, $R^c$, $R^d$, $R^e$ and $R^g$ are hydrogen atoms, (3) $R^g$ must not be a methyl group when $R^b$, $R^c$, $R^e$ and $R^f$ are hydrogen atoms, and $R^a$ is a hydrogen atom or an acetyl group, (4) $R^b$ and $R^f$ must not be methyl groups when $R^a$, $R^c$, $R^d$, $R^d$, $R^e$ and $R^g$ are hydrogen atoms, (5) $R^b$ must not be an allyl group when $R^c$, $R^d$, $R^e$, $R^f$ and $R^g$ are hydrogen atoms, and $R^a$ is a hydrogen atom or an acetyl group, (6) any one to three of $R^b$ to $R^g$ must not be lower alkyl groups or halogen atoms when $R^a$ is a hydrogen atom, (7) $R^a$ must not be a hydrogen atom and an acetyl group when $R^b$, $R^c$, $R^d$, $R^e$, $R^f$ and $R^g$ are hydrogen atoms, (8) $R^f$ must not be a cyano-substituted lower alkyl group when $R^a$, $R^b$, $R^c$, $R^d$, $R^e$ and $R^g$ are hydrogen atoms, and (9) any one of $R^d$, $R^e$, $R^f$ and $R^g$ must not be a hydrogen atom when $R^b$ and $R^c$ are hydrogen atoms and any one of $R^d$, $R^e$, $R^f$ and $R^g$ is a lower alkenyl group];

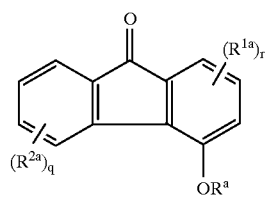

[wherein $R^a$ is as defined above; q is an integer of 1 to 4; r is an integer of 1 to 3;

$R^{1a}$ has the same meanings as $R^b$ and $R^c$ defined above;
$R^{2a}$ has the same meanings as $R^d$ to $R^e$ defined above;
provided that,
(1) $R^{1a}$ must not be a hydrogen atom when $R^a$ is a hydrogen atom or an acetyl group and $R^{2a}$ is a lower alkoxy group,
(2) $R^{2a}$ must not be a lower alkenyl group when $R^{1a}$ is a hydrogen atom and q is 1, and
(3) a total of r and q must not be an integer of 2 to 4 when $R^a$ is a hydrogen atom and $R^{1a}$ and $R^{2a}$ indicate a hydrogen atom, a halogen atom or a lower alkyl group];

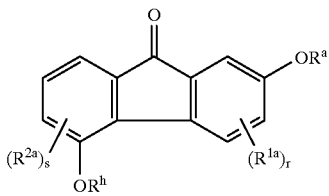

[wherein $R^{1a}$, $R^{2a}$, $R^a$ and r are as defined above; $R^h$ is a hydrogen atom, a lower alkenyl group or an acetyl group; s is an integer of 1 to 3; provided that,
(1) any one of $R^a$ and $R^h$ is an acetyl group when $R^{1a}$ and $R^{2a}$ are hydrogen atoms, and
(2) a 4-position of a fluorenone skeleton must not be substituted with $R^{1a}$ when $R^a$ and $R^h$ are hydrogen atoms or acetyl groups and $R^{2a}$ is a hydrogen atom, r is 1 and $R^{1a}$ is a methoxy group]; and

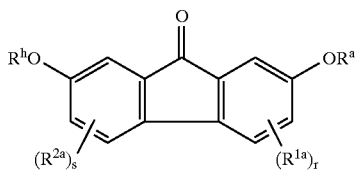

[wherein $R^{1a}$, $R^{2a}$, $R^a$, $R^h$, r and s are as defined above; provided that,
(1) both $R^{1a}$ and $R^{2a}$ must not be hydrogen atoms when $R^a$ and $R^h$ are hydrogen atoms or acetyl groups,
(2) 1- and 8-positions of a fluorenone skeleton must not be substituted with $R^{1a}$ and $R^{2a}$ when $R^a$ and $R^h$ are hydrogen atoms, r and s are 1 and $R^{1a}$ and $R^{2a}$ are methyl groups, and
(3) 3- and 6-positions of a fluorenone skeleton must not be substituted with $R^{1a}$ and $R^{2a}$ when $R^a$ and $R^h$ are hydrogen atoms, r and s are 1 and $R^{1a}$ and $R^{2a}$ are halogen atoms].

The central and/or peripheral nerve cells degeneration repair or protective agent of the present invention contains a fluorenone derivative represented by the formula:

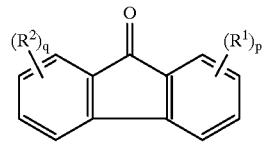

[wherein $R^1$ is a hydrogen atom, a hydroxyl group, a lower alkenyl group, a lower alkyl group, a halogen atom, a lower alkoxy group, a lower alkylthio group, a lower alkanoyloxy group, a lower alkenyloxy group, a group of the formula:

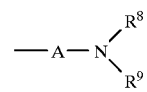

(wherein $R^8$ and $R^9$ are as defined above), an imidazolyl-substituted lower alkyl group, a lower alkoxy-substituted lower alkyl group, a hydroxyl group-substituted lower alkoxy-lower alkoxy-substituted lower alkyl group or a lower trialkyl-substituted ammonium-substituted lower alkyl group;

$R^2$ is a hydrogen atom, a hydroxyl group, a lower alkenyl group, a lower alkyl group, a halogen atom, a lower alkoxy group, a lower alkanoyloxy group, a lower alkenyloxy group, a group of the formula:

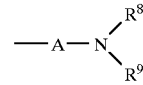

(wherein $R^8$, $R^9$ and A are as defined above), an imidazolyl-substituted lower alkyl group, a lower alkoxy-substituted lower alkyl group, a pyridylthio-substituted lower alkyl group, a phenylthiothio-substituted lower alkyl group optionally containing a lower alkoxy group as a substituent on a phenyl ring, a benzimidazolylthio-substituted lower alkyl group, an imidazolylthio-substituted lower alkyl group, a lower alkanoyl group, a cycloalkylthio-substituted lower alkyl group, a cyano-substituted lower alkyl group or a lower trialkyl-substituted ammonium-substituted lower alkyl group;

p and q indicate an integer of 1 to 4; and
$R^1$ and $R^2$ may be the same or different] as an active component.

The fluorenone derivative represented by the above formula (1) has an action of extremely accelerating survival of nerve cells and stretching of neulite and further increasing enzyme activity of choline acetyltransferase (CHAT) as an acetylcholine synthesis enzyme of colinergic nerve cells. Accordingly, the compound represented by the above formula (1) has particularly an action of accelerating survival and growth of colinergic nerve cells of a central nervous system and a protective action against the disorder thereof.

Further, the fluorenone derivative represented by the above formula (1) has a peripheral nerve degeneration repair or protective action and is useful as a peripheral nerve degeneration repair or protective agent. For example, it is useful as an effective remedy for neuropathy due to injury, neuropathy due to metabolic factor such as diabetic neuropathy, neuropathy caused by side effect of poison or drug, peripheral neuropathy such as multiple neuritis and the like.

An enzyme is essential to life-sustaining of a living body, e.g. energy production, metabolism, etc. The enzyme becomes a so-called active enzyme such as oxygen anion radical, peroxidized ion, hydroxy radical, etc. by the reaction in energy production system, enzyme reaction, reaction due to ultraviolet rays, radiation, etc. The active oxygen species are useful for the living body in view of bactericidal action of oxygenase, white blood cells and the like. On the other hand, they accelerate hyperoxidation of an unsaturated fatty acid forming phospholipid of biomembrane, such as oleic acid, linolic acid, linolenic acid, arachidonic acid, etc. to form lipoperoxide. The resulting lipoperoxide cause formation of alkoxy radical and hydroxy radical, similar to the above active oxygen species to attach the biomembrane, which results in membrane disorder and devitalization of various useful enzymes [see Metabosilm 15 (10), 1978, special issue of "Active Oxygen"].

In the living body, for example, enzymes having something to do with metabolic devitalization of the above active oxygen species, such as superoxide dismutase (SOD), catalase, glutathione peroxidase, etc. are present, and vitamins having various antioxidation capacities are also present, in addition to α-tocopherol (vitamin E). According to the action of these enzymes and vitamins, normal life-sustaining can be conducted. However, failure is arisen in a suitable defensive mechanism due to the above enzymes and vitamins for some reason, or formation of the active oxygen species which surpass a capacity of the defensive mechanism or formation/accumulation of lipoperoxide is sometimes recognized. When such a failure is arisen in the defensive mechanism, serious disorders such as various diseases due to platelet aggregation, inflammation, hepatopathy, arterial sclerosis, cythemolysis, aging or senile dementia, retinopaty, pulmonary disturbance, cardiac/pulmonary disturbance due to certain drug, ischemic angiopathy and the like are arisen with the chain reactive progress of the hyperoxidation reaction.

A compound having an action of scavenging active oxygen species (radical) which have hitherto been considered to be a main factor of the above various disorders and preventing or reducing formation/accumulation of lipoperoxide in the living body is normally referred to as an antioxidant. Actually, several examples of the preventive and therapeutic effect thereof on the above various diseases have been reported. As the reported antioxidant, for example, there are enzyme including the above SOD [Superoxide and Medical, Yoshihiko Oyanagi, 1981, Kyoritsu Shuppansha, pages 137–141], butylated hydroxytoluene (BHT), butylated hydroxyanisol (BHA), α-tocopherol (vitamin E) [Makoto Mino and Hidetaka Tanaka, Medicinal Journal, 19 (12), 1983, pages 2351–2359; and Toshihiko Suematsu, Medicinal Journal, 19 (5), 1983, pages 909–914] and the like.

The fluorenone derivative represented by the above formula (1) (hereinafter referred to as a "compound of the present invention") has an action of scavenging active oxygen species and preventing/reducing formation of lipoperoxide in the living body. Accordingly, the compound of the present invention is useful as a preventive or a remedy for various disorders/diseases caused by the overformation of the above active oxygen species, accumulation of lipoperoxide in the living body or failure of the defensive mechanism against them. For example, it is also useful as medicines such as antiarteriosclerotic agent, carcinogenesis preventive, anti-inflammatory agent, analgesic, autoimmune disease remedy, platelet aggregation inhibitor, hypotensive drug, antilipemic agent, preventive and remedy for prematurity retinopathy and cataract and the like. Further, the compound of the present invention is not only useful as the above medicines, but also useful as antioxidants for fats and oils contained in processed foods.

Further, the compound of the present invention has a cyclic guanosine 3', 5'-monophosphate-phosphodiesterase (c-GMP-PDE) inhibition action, and also has an antiplatelet action, antineutrophil action, antivasospasm action, angiectasia action and effect-enhancing action of EDRF (endothelium-derived relaxing factor) and nitro-based vasodialtor by increasing c-GMP concentration.

Accordingly, the compound of the present invention is useful for treating and preventing diseases such as stable/unstable type angina pectoris, hypertension, tenal hypertension, congestive heart failure, arterial sclerosis, peripheral angiopathy, e.g. post PTCA (post-percutaneous transluminal coronary angioplastry), cerebral hemorrhage, bronchitis, chronic asthma, allergic asthma, allergic rhinitis, glaucoma and the like.

Examples of the respective groups defined in the present specification are as follows.

Examples of the lower alkyl group include straight- or branched-chain alkyl groups having 1 to 6 carbon atoms such as methyl, ethyl, propyl, isopropyl, butyl, tert-butyl, pentyl, hexyl groups and the like.

Examples of the lower alkenyl group include straight- or branched-chain alkenyl groups having 2 to 6 carbon atoms such as vinyl, allyl, 2-butenyl, 3-butenyl, 1-methylallyl, 2-pentenyl, 2-hexenyl groups and the like.

Examples of the halogen atom include fluorine, chlorine, bromine and iodine atoms and the like.

Examples of the lower alkoxy group include straight- or branched-chain alkoxy groups having 1 to 6 carbon atoms such as methoxy, ethoxy, propoxy, isopropoxy, butoxy, tert-butoxy, pentyloxy, hexyloxy groups and the like.

Examples of the lower alkylthio group include straight- or branched-chain alkylthio groups having 1 to 6 carbon atoms such as methylthio, ethylthio, propylthio, isopropylthio, butylthio, tert-butylthio, pentylthio, hexylthio groups and the like.

Examples of the lower alkanoyloxy group include straight- or branched-chain alkanoyloxy groups having 1 to 6 carbon atoms such as formyloxy, acetyloxy, propionyloxy, butyryloxy, isobutyryloxy, pentanoyloxy, tert-butylcarbonyloxy, hexanoyloxy groups and the like.

Examples of the lower alkenyloxy group include straight- or branched-chain alkenyloxy groups having 2 to 6 carbon atoms such as vinyloxy, allyloxy, 2-butenyloxy, 3-butenyloxy, 1-methylallyloxy, 2-pentenyloxy, 2-hexenyloxy groups and the like.

Examples of the lower alkoxycarbonyl-substituted lower alkyl group include straight- or branched-chain alkoxycarbonylalkyl groups having 1 to 6 carbon atoms in each of which alkoxycarbonyl moiety is a straight- or branched-chain alkoxycarbonyl group having 1 to 6 carbon atoms, such as methyoxycarbonylmethyl, 3-methoxycarbonylpropyl, ethoxycarbonylmethyl, 3-ethoxycarbonylpropyl, 4-ethoxycarbonylbutyl, 5-isopropoxycarbonylpentyl, 6-propoxycarbonylhexyl, 1,1-dimethyl-2-butoxycarbonylethyl, 2-methyl-3-tert-butoxycarbonylpropyl, 1-methoxycarbonylisopentyl, 2-pentyloxycarbonylethyl, hexyloxycarbonylmethyl groups and the like.

Examples of the lower alkoxycarbonyl group include straight- or branched-chain alkoxycarbonyl groups having 1 to 6 carbon atoms such as methoxycarbonyl, ethoxycarbonyl, propoxycarbonyl, isopropoxycarbonyl, butoxycarbonyl, tert-butoxycarbonyl, pentyloxycarbonyl, hexyloxycarbonyl groups and the like.

Examples of the 5- or 6-membered saturated heterocycle formed by bonding $R^8$ and $R^9$ together with the nitrogen atom to which they are attached through a nitrogen or oxygen atom or not include pyrrolidinyl, piperidinyl, piperazinyl, morpholino groups and the like.

Examples of the heterocycle group substituted with a substituent selected from the group consisting of a lower alkyl group and a lower alkoxycarbonyl group include the heterocycle groups substituted with 1 to 3 susbtituents selected from the group consisting of a straight- or branched-chain alkyl group having 1 to 6 carbon atoms and a straight- or branched-chain alkoxycarbonyl group having 1 to 6 carbon atoms, such as 4-methylpiperazinyl, 3,4-dimethylpiperazinyl, 3-ethylpyrrolidinyl, 2-propylpyrrolidinyl, 3,4,5-trimethylpiperidinyl, 4-butylpiperidinyl, 3-pentylmorpholino, 4-hexylpiperazinyl, 4-ethoxycarbonylpiperazinyl, 3-methoxycarbonylmorpholino, 3-methyl-4-ethoxycarbonylpiperidinyl, 2-methoxycarbonylpyrrolidinyl, 3-ethoxycarbonylpyrrolidinyl groups and the like.

Examples of the imidazolyl-substituted lower alkyl group include imidazolyl-substituted alkyl groups in each of which alkyl moiety is a straight- or branched-chain alkyl group having 1 to 6 carbon atoms, such as (1-imidazolyl)methyl, 2-(1-imidazolyl)ethyl, 1-(2-imidazolyl)ethyl, 3-(4-imidazolyl)propyl, 4-(5-imidazolyl)butyl, 5-(1-imidazolyl)pentyl, 6-(2-imidazolyl)hexyl, 1,1-dimethyl-2-(1-imidazolyl)ethyl, 2-methyl-3-(1-imidazolyl)propyl groups and the like.

Examples of the lower alkoxy-lower alkyl group include straight- or branched-chain alkoxyalkyl groups having 1 to 6 carbon atoms in each of which alkyl moiety is a straight- or branched-chain alkyl group having 1 to 6 carbon atoms, such as methoxymethyl, 2-ethoxymethyl, 1-methoxymethyl, 3-methoxypropyl, 4-ethoxybutyl, 6-propoxyhexyl, 5-isopropoxypentyl, 1,1-dimethyl-2-butoxyethyl, 2-methyl-3-tert-butoxypropyl, 2-pentyloxyethyl, hexyloxymethyl groups and the like.

Examples of the lower alkylene group include straight- or branched-chain alkylene groups having 1 to 6 carbon atoms such as methylene, ethylene, trimethylene, 2-methyltrimethylene, 2,2-dimethyltrimethylene, 1-methyltrimethylene, methylmethylene, ethylmethylene, tetramethylene, pentamethylene, hexamethylene groups and the like.

Examples of the pyridylthio-substituted lower alkyl group include pyridylthio-substituted alkyl groups in each of which alkyl moiety is a straight- or branched-chain alkyl group having 1 to 6 carbon atoms, such as (2-pyridyl)thiomethyl, (3-pyridyl)thiomethyl, (4-pyridyl)thiomethyl, 2-(2-pyridyl)thioethyl, 2-(3-pyridyl)thioethyl, 2-(4-pyridyl)thioethyl, 3-(2-pyridyl)thiopropyl, 3-(3-pyridyl)thiopropyl, 3-(4-pyridyl)thiopropyl, 4-(2-pyridyl)thiobutyl, 4-(3-pyridyl)thiobutyl, 4-(4-pyridyl)thiobutyl, 5-(2-pyridyl)thiopentyl, 5-(3-pyridyl)thiopentyl, 5-(4-pyridyl)thiopentyl, 6-(2-pyridyl)thiohexyl, 6-(3-pyridyl)thiohexyl, 6-(4-pyridyl)thiohexyl, 1,1-dimethyl-2-(2-pyridyl)thioethyl, 1,1-dimethyl-2-(3-pyridyl)thioethyl, 1,1-dimethyl-(4-pyridyl)thioethyl, 2-methyl-3-(2-pyridyl)thiopropyl, 2-methyl-3-(3-pyridyl)thiopropyl, 2-methyl-3-(4-pyridyl)thiopropyl groups and the like.

Examples of the phenylthio-lower alkyl group optionally containing a lower alkoxy group as a substituent on a phenyl ring include phenylthio alkyl groups in each of which alkyl ring moiety optionally containing 1 to 3 straight- or branched-chain alkoxy groups having 1 to 6 carbon atoms as a substituent on a phenyl ring is a straight- or branched chain alkyl group having 1 to 6 carbon atoms, such as phenylthiomethyl, 1-phenylthioethyl, 2-phenylthioethyl, 1-phenylthioethyl, 3-phenylthiopropyl, 4-phenylthiobutyl, 5-phenylthiopentyl, 6-phenylthiohexyl, 1,1-dimethyl-2-phenylthioethyl, 2-methyl-3-phenylthiopropyl, (2-methoxyphenyl)thiomethyl, (3-methoxyphenyl)thiomethyl, (4-methoxyphenyl)thiomethyl, 2-(4-methoxyphenyl)thioethyl, 1-(2-ethoxyphenyl)thioethyl, 3-(4-isopropoxyphenyl)thiopropyl, 4-(3-pentyloxyphenyl)thiobutyl, 5-(4-hexyloxyphenyl)thiopentyl, 6-(2-butyloxyphenyl)thiohexyl, (3,4-dimethoxyphenyl)thiomethyl, (3-ethoxy-4-methoxyphenyl)thiomethyl, (2,3-dimethoxyphenyl)thiomethyl, (2,6-dimethoxyphenyl)thiomethyl, (3,4,5-trimethoxyphenyl)thiomethyl groups and the like.

Examples of the benzimidazolylthio-substituted lower alkyl group include benzimidazolylthio-substituted straight- or branched chain alkyl groups having 1 to 6 carbon atoms such as (benzimidazole-2-yl)thiomethyl, 1-(benzimidazole-4-yl)thioethyl, 2-(benzimidazole-5-yl)thioethyl, 3-(benzimidazole-6-yl)thiopropyl, 4-(benzimidazole-2-yl)thiobutyl, 5-(benzimidazole-7-yl)thiopentyl, 6-(benzimidazole-2-yl)thiohexyl, 1,1-dimethyl-2-(benzimidazole-2-yl)thioethyl, 2-methyl-3-(benzimidazole-2-yl)thiopropyl groups and the like.

Examples of the imidazolylthio-substituted lower alkyl group include imidazolylthio-substituted alkyl groups in each of which alkyl moiety is a straight- or branched-chain alkyl group having 1 to 6 carbon atoms, such as (2-imidazolyl)thiomethyl, 2-(2-imidazolyl)thioethyl, 1-(2-imidazolyl)thioethyl, 3-(4-imidazolyl)thiopropyl, 4-(5-imidazolyl)thiobutyl, 5-(4-imidazolyl)thiopentyl, 6-(2-imidazolyl)thiohexyl, 1,1-dimethyl-2-(2-imidazolyl)thiohexyl, 1,1-dimethyl-2-(2-imidazolyl)thioethyl, 2-methyl-3-(5-imidazolyl)thiopropyl groups and the like.

Examples of the lower alkanoyl group include straight- or branched chain alkanoyl group having 1 to 6 carbon atoms such as formyl, acetyl, propionyl, butyryl, isobutyryl, pentanoyl, tert-butylcarbonyl, hexanoyl groups and the like.

Examples of the cycloalkylthio-substituted lower alkyl group include cycloalkylthioalkyl groups having 3 to 8 carbon atoms in each of which alkyl moiety is a straight- or branched-chain alkyl group having 1 to 6 carbon atoms, such as cyclopropylthioethyl, 2-cyclobutylthioethyl, 1-cyclopentylthioethyl, 3-cyclohexylthiopropyl, cyclohexylthiomethyl, 4-cycloheptylthiobutyl, 5-cyclooctylthiopentyl, 6-cyclohexylthiohexyl, 1,1-dimethyl-2-cyclohexylthioethyl, 2-methyl-3-cyclohexylthiopropyl groups and the like.

Examples of the cyano-substituted lower alkyl group include cyanoalkyl groups in each of which alkyl moiety is a straight- or branched-chain alkyl group having 1 to 6 carbon atoms, such as cyanomethyl, 2-cyanoethyl, 1-cyanoethyl, 3-cyanopropyl, 4-cyanobutyl, 5-cyanopentyl, 6-cyanohexyl, 1,1-dimethyl-2-cyanoethyl, 2-methyl-3-cyanopropyl groups and the like.

Examples of the hydroxyl group-substituted lower alkoxy-lower alkoxy-substituted lower alkyl group include straight- or branched-chain alkoxy group having 1 to 6 carbon atoms (containing 1 to 3 hydroxyl groups)-substituted straight- or branched chain alkoxy group having 1 to 6 carbon atoms-substituted straight- or branched-chain alkyl groups having 1 to 6 carbon atoms, such as 2-[2-(2-hydroxyethoxy)ethoxy]propyl, hydroxymethoxymethoxymethyl, 2-[3-(2-hydroxyethoxy)propoxy]ethyl, [(3,4,5-trihydroxypentyloxy)methoxy]methyl, 1-[4-(1-hydroxyethoxy)butoxy]ethyl, 3-[6-(3-hydroxypropoxy)hexyloxy]propyl, 4-[5-(2,3-dihydroxypropoxy)pentyloxy]butyl, 5-[1,1-dimethyl-2-(4-hydroxybutoxy)ethoxy]pentyl, 6-[2-methyl-3-(3,4-dihydroxybutoxy)propoxy]hexyl, [2-(1,1-dimethyl-2-hydroxyethoxy)ethoxy]methyl, 2-[(5-hydroxypentyloxy)methoxy]ethyl, 3-(6-hydroxyhexyloxymethoxy)propyl, [(2-methyl-3-hydroxypropoxy)methoxy]methyl groups and the like.

Examples of the lower trialkyl-substituted ammonium-substituted lower alkyl group include ammonium alkyl groups in each of which lower alkyl moiety having 3 straight- or branched chain alkyl groups having 1 to 6 carbon atoms is a straight- or branched-chain alkyl group having 1 to 6 carbon atoms, such as trimethylammoniummethyl, 2-(triethylammonium)ethyl, 1-(tripropylammonium)ethyl, 3-(tributylammonium)propyl, 4-(tripentylammonium)butyl, 5-(triethylammonium)pentyl, 6-(trihexylammonium)hexyl, 1,1-dimethyl-2-(N-methyl-N-ethyl-N-propylammonium)ethyl, 2-methyl-3-(N,N-dimethyl-N-ethylammonium)propyl, 3-(N-propyl-N,N-dimethylammonium)propyl, 4-(N,N-dihexyl-N-methylammonium)butyl, 5-(N-pentyl-N-methyl-N-ethylammonium)pentyl, 6-(N-butyl-N-methyl-N-ethylammonium)hexyl groups and the like.

The following compounds of various embodiments are included in the fluorenone derivative of the formula (1) as an active component of the central or peripheral nerve degeneration repair or protective agent of the present invention.

(1) A fluorenone derivative wherein $R^1$ is a hydroxyl group, a lower alkenyl group, a lower alkyl group, a halogen atom, a lower alkylthio group, a group of the formula:

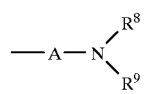

(wherein A, $R^8$ and $R^9$ are the same as those defined in the above formula (A)), an imidazolyl-substituted lower alkyl group, a lower alkoxy-substituted lower alkyl group, a hydroxyl group-substituted lower alkoxy-lower alkoxy-substituted lower alkyl group or a lower trialkyl-substituted ammonium-substituted lower alkyl group; $R^2$ is a hydroxyl group, a lower alkenyl group, a lower alkyl group, a halogen atom, a group of the formula:

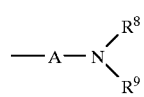

(wherein A, $R^8$ and $R^9$ are the same as those defined in the above formula (A)), an imidazolyl-substituted lower alkyl group, a lower alkoxy-substituted lower alkyl group, a pyridylthio-substituted lower alkyl group, a phenylthio-substituted lower alkyl group optionally containing a lower alkoxy group as a substituent on a phenyl ring, a benzimidazolylthio-substituted lower alkyl group, an imidazolylthio-substituted lower alkyl group, a lower alkanoyl group, a cycloalkylthio-substituted lower alkyl group, a cyano-substituted lower alkyl group or a lower trialkyl-substituted ammonium-substituted lower alkyl group, or a salt thereof.

(2) A fluorenone derivative wherein $R^1$ is a hydrogen atom, a lower alkenyl group, a lower alkyl group, a halogen atom, a lower alkoxy group, a lower alkylthio group, a lower alkanoyloxy group or a lower alkenyloxy group; and $R^2$ is the same as that defined in the above item (1), or a salt thereof.

(3) A fluorenone derivative wherein $R^1$ is the same as that defined in the above item (2); and $R^2$ is a hydrogen atom, a lower alkenyl group, a lower alkyl group, a halogen atom, a lower alkoxy group, a lower alkanoyloxy group or a lower alkenyloxy group, or a salt thereof.

(4) A fluorenone derivative wherein $R^1$ is the same as that defined in the above item (1); and $R^2$ is the same as that defined in the above item (3), or salt thereof.

(5) A fluorenone derivative wherein $R^1$ is a lower alkenyl group, a lower alkyl group, a halogen atom, a lower alkoxy group, a lower alkylthio group, a lower alkanoyloxy group, a lower alkenyloxy group, a hydroxyl group, a group of the formula:

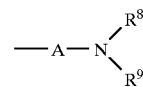

(wherein A, $R^8$ and $R^9$ are the same as those defined in the above formula (A)), an imidazolyl-substituted lower alkyl group, a lower alkoxy-substituted lower alkyl group, a hydroxyl group-substituted lower alkoxy-lower alkoxy-substituted lower alkyl group or a lower trialkyl-substituted ammonium-substituted lower alkyl group; $R^2$ is a lower alkenyl group, a lower alkyl group, a halogen atom, a lower alkoxy group, a lower alkanoyloxy group, a lower alkenyloxy group, a hydroxyl group, a group of the formula:

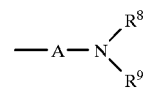

(wherein A, $R^8$ and $R^9$ are the same as those defined in the above formula (A)), an imidazolyl-substituted lower alkyl group, a lower alkoxy-substituted lower alkyl group, a pyridylthio-substituted lower alkyl group, a phenylthio-substituted lower alkyl group optionally containing a lower alkoxy group as a substituent on a phenyl ring, a benzimidazolylthio-substituted lower alkyl group, an imidazolylthio-substituted lower alkyl group, a lower alkanoyl group, a cycloalkylthio-substituted lower alkyl group, a cyano-substituted lower alkyl group or a lower trialkyl-substituted ammonium-substituted lower alkyl group, or a salt thereof.

(6) A fluorenone derivative wherein $R^1$ is the same as that defined in the above item (5); and $R^2$ is the same as that defined in the above item (1), or salt thereof.

(7) A fluorenone derivative wherein $R^1$ is the same as that defined in the above item (5); and $R^2$ is the same as that defined in the above item (3), or salt thereof.

(8) A fluorenone derivative wherein $R^1$ is the same as that defined in the above item (1); and $R^2$ is the same as that defined in the above item (5), or salt thereof.

(9) A fluorenone derivative wherein $R^1$ is the same as that defined in the above item (2); and $R^2$ is the same as that defined in the above item (5), or salt thereof.

(10) A fluorenone derivative wherein $R^1$ is a lower alkoxy group, a lower alkanoyloxy group or a lower alkenyloxy group; and $R^2$ is a lower alkoxy group, a lower alkanoyloxy group or a lower alkenyloxy group, or a salt thereof.

(11) A fluorenone derivative wherein $R^1$ is a lower alkenyl group, a lower alkyl group, a halogen atom or a lower alkylthio group; and $R^2$ is a lower alkenyl group, a lower alkyl group or a halogen atom, or a salt thereof.

(12) A fluorenone derivative wherein $R^1$ is a hydroxyl group, a group of the formula:

$$-A-N\begin{matrix}R^8\\R^9\end{matrix}$$

(wherein A, $R^8$ and $R^9$ are the same as those defined in the above formula (A)), an imidazolyl-substituted lower alkyl group, a lower alkoxy-substituted lower alkyl group, a hydroxyl group-substituted lower alkoxy-lower alkoxy-substituted lower alkyl group or a lower trialkyl-substituted ammonium-substituted lower alkyl group; $R^2$ is a hydroxyl group, a group of the formula:

$$-A-N\begin{matrix}R^8\\R^9\end{matrix}$$

(wherein A, $R^8$ and $R^9$ are the same as those defined in the above formula (A)), an imidazolyl-substituted lower alkyl group, a lower alkoxy-substituted lower alkyl group, a pyridylthio-substituted lower alkyl group, a phenylthio-substituted lower alkyl group optionally containing a lower alkoxy group as a substituent on a phenyl ring, a benzimidazolylthio-substituted lower alkyl group, an imidazolylthio-substituted lower alkyl group, a lower alkanoyl group, a cycloalkylthio-substituted lower alkyl group, a cyano-substituted lower alkyl group or a lower trialkyl-substituted ammonium-substituted lower alkyl group, or a salt thereof.

(13) A fluorenone derivative wherein $R^1$ is the same as that defined in the above item (10); and $R^2$ is the same as that defined in the above item (1), or salt thereof.

(14) A fluorenone derivative wherein $R^1$ is the same as that defined in the above item (10); and $R^2$ is the same as that defined in the above item (3), or salt thereof.

(15) A fluorenone derivative wherein $R^1$ is the same as that defined in the above item (10); and $R^2$ is the same as that defined in the above item (5), or salt thereof.

(16) A fluorenone derivative wherein $R^1$ is the same as that defined in the above item (10); and $R^2$ is the same as that defined in the above item (11) or salt thereof.

(17) A fluorenone derivative wherein $R^1$ is the same as that defined in the above item (10); and $R^2$ is the same as that defined in the above item (12), or salt thereof.

(18) A fluorenone derivative wherein $R^1$ is the same as that defined in the above item (11); and $R^2$ is the same as that defined in the above item (1), or salt thereof.

(19) A fluorenone derivative wherein $R^1$ is the same as that defined in the above item (11); and $R^2$ is the same as that defined in the above item (3), or salt thereof.

(20) A fluorenone derivative wherein $R^1$ is the same as that defined in the above item (11); and $R^2$ is the same as that defined in the above item (5), or salt thereof.

(21) A fluorenone derivative wherein $R^1$ is the same as that defined in the above item (11); and $R^2$ is the same as that defined in the above item (10), or salt thereof.

(22) A fluorenone derivative wherein $R^1$ is the same as that defined in the above item (11); and $R^2$ is the same as that defined in the above item (12), or salt thereof.

(23) A fluorenone derivative wherein $R^1$ is the same as that defined in the above item (12); and $R^2$ is the same as that defined in the above item (1), or salt thereof.

(24) A fluorenone derivative wherein $R^1$ is the same as that defined in the above item (12); and $R^2$ is the same as that defined in the above item (3), or salt thereof.

(25) A fluorenone derivative wherein $R^1$ is the same as that defined in the above item (12); and $R^2$ is the same as that defined in the above item (5), or salt thereof.

(26) A fluorenone derivative wherein $R^1$ is the same as that defined in the above item (12); and $R^2$ is the same as that defined in the above item (11), or salt thereof.

(27) A fluorenone derivative wherein $R^1$ is the same as that defined in the above item (12); and $R^2$ is the same as that defined in the above item (10), or salt thereof.

(28) A fluorenone derivative wherein $R^1$ is the same as that defined in the above item (1); and $R^2$ is the same as that defined in the above item (10), or salt thereof.

(29) A fluorenone derivative wherein $R^1$ is the same as that defined in the above item (2); and $R^2$ is the same as that defined in the above item (10), or salt thereof.

(30) A fluorenone derivative wherein $R^1$ is the same as that defined in the above item (5); and $R^2$ is the same as that defined in the above item (10), or salt thereof.

(31) A fluorenone derivative wherein $R^1$ is the same as that defined in the above item (11); and $R^2$ is the same as that defined in the above item (10), or salt thereof.

(32) A fluorenone derivative wherein $R^1$ is the same as that defined in the above item (12); and $R^2$ is the same as that defined in the above item (10) or salt thereof.

(33) A fluorenone derivative wherein $R^1$ is the same as that defined in the above item (1); and $R^2$ is the same as that defined in the above item (11), or salt thereof.

(34) A fluorenone derivative wherein $R^1$ is the same as that defined in the above item (2); and $R^2$ is the same as that defined in the above item (11), or salt thereof.

(35) A fluorenone derivative wherein $R^1$ is the same as that defined in the above item (5); and $R^2$ is the same as that defined in the above item (11), or salt thereof.

(36) A fluorenone derivative-wherein $R^1$ is the same as that defined in the above item (10); and $R^2$ is the same as that defined in the above item (11), or salt thereof.

(37) A fluorenone derivative wherein $R^1$ is the same as that defined in the above item (12); and $R^2$ is the same as that defined in the above item (11), or salt thereof.

(38) A fluorenone derivative wherein $R^1$ is the same as that defined in the above item (1); and $R^2$ is the same as that defined in the above item (12), or salt thereof.

(39) A fluorenone derivative wherein $R^1$ is the same as that defined in the above item (2); and $R^2$ is the same as that defined in the above item (12), or salt thereof.

(40) A fluorenone derivative wherein $R^1$ is the same as that defined in the above item (5); and $R^2$ is the same as that defined in the above item (12), or salt thereof.

(41) A fluorenone derivative wherein $R^1$ is the same as that defined in the above item (10); and $R^2$ is the same as that defined in the above item (12), or salt thereof.

(42) A fluorenone derivative wherein $R^1$ is the same as that defined in the above item (11); and $R^2$ is the same as that defined in the above item (12), or salt thereof.

The fluorenone derivative represented by the formula (1) may be produced by various methods, for example, it is easily produced by a method shown in the following reaction scheme.

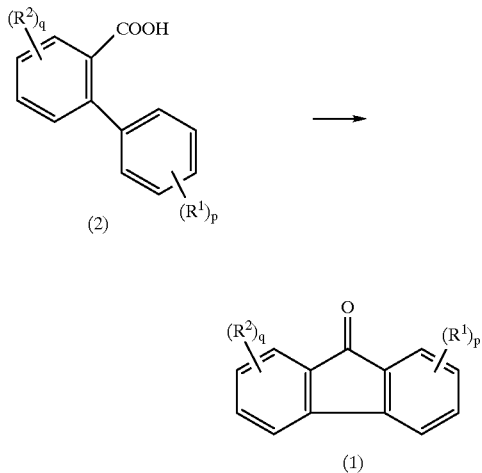

[wherein $R^1$, $R^2$, p and q are as defined above].

The cyclization reaction of introducing the compound (2) to the compound (1) can be conducted by various cyclization reactions which have hitherto been known. Examples thereof include a method due to heating, a cyclization method using acidic substances such as phosphorous oxychloride, phosphorous pentachloride, phosphorous trichloride, thionyl chloride, concentrated sulfuric acid, polyphosphoric acid and the like. When employing the cyclization method due to heating, high boiling point hydrocarbons and high boiling point ethers, e.g. solvents such as tetralin, diphenyl ether, diethylene glycol dimethyl ether and the like are used. Normally, the heating condition of 100 to 250° C., preferably 150 to 200° C. can be employed. When employing the cyclization method using the acidic substance, the proportion of the acidic substance to the compound (2) is normally in a range from an equimolar amount to an excessive amount, preferably from 10- to 20-time molar amount. Normally, the reaction may be conducted at a temperature from room temperature to 150° C. for about 0.1 to 6 hours. In case of the cyclization method using the acidic substance, the reaction may be conducted under the absence or presence of a suitable solvent. As the solvent, there can be used any one as far as it exerts no influence upon the reaction, and examples thereof include ethers such as diethyl ether, dioxane, tetrahydrofuran, monoglyme, diglyme, etc.; acid anhydrides such as acetic anhydride, etc.; aliphatic hydrocarbons such as n-hexane, heptane, ligroin, etc,; halogenated hydrocarbons such as chloroform, methylene chloride, carbon tetrachloride, etc.; aprotic polar solvents such as dimethylformamide, dimethyl sulfoxide, hexamethylphosphoric triamide, etc.

The compound (2) used as a starting material can be produced by a method shown in the following reaction scheme-2.

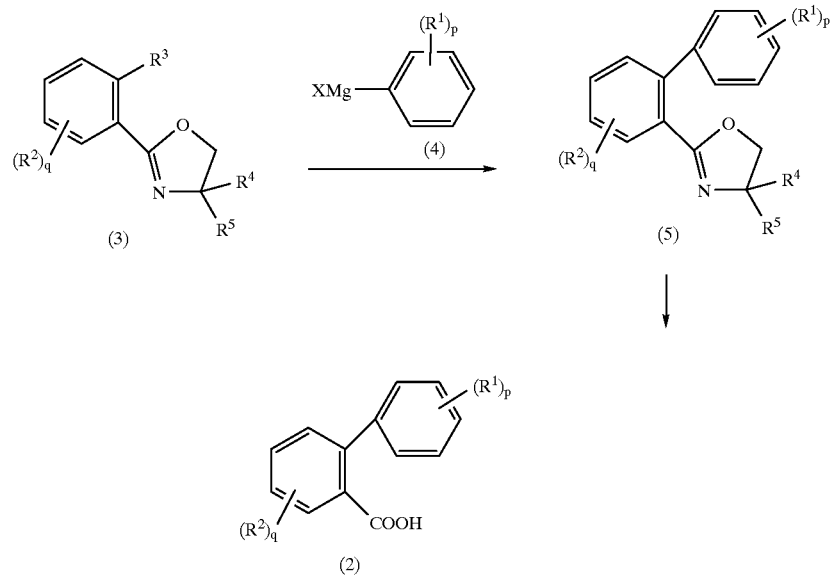

[wherein $R^1$, $R^2$, p and q are as defined above; $R^3$ is a lower alkoxy group; X is a halogen atom; and $R^4$ and $R^5$ are the same or different and indicate a lower alkyl group].

The reaction between the compound (3) and the compound (4) is conducted in a suitable solvent. As the solvent, there can be any one which is used in a Grignard reaction. Preferred examples thereof include ethers such as diethyl ether, dioxane, tetrahydrofuran, etc.; aromatic hydrocarbons such as benzene, toluene, etc.; saturated hydrocarbons such as pentane, hexane, heptane, cyclohexane, etc. The proportion of the compound (4) to the compound (3) is normally at least an equimolar amount, preferably in a range from an equimolar amount to 2-time molar amount. The above reaction is normally conducted at a temperature from about −70 to 50° C., preferably from −30° C. to room temperature. Normally, it is completed for about 1 to 50 hours.

The reaction of introducing the compound (5) to the compound (2) is conducted by alkylating the compound (5) in a suitable solvent in the presence of an alkylating agent and hydrolyzing the resulting compound.

As the alkylating agent used for alkylating the compound (5), for example, there is a halogenated alkyl such as methyl iodide and the like. The alkylation is normally conducted at a temperature from room temperature to 200° C., preferably from room temperature to 150° C. Normally, it is completed for about 1 to 30 hours. Examples of the solvent include ethers such as dioxane, tetrahydrofuran, ethylene glycol dimethyl ether, diethyl ether, etc.; aromatic hydrocarbons such as benzene, toluene, xylene, etc.; halogenated hydrocarbons such as dichloromethane, chloroform, carbon tetrachloride, etc.; lower alcohols such as methanol, ethanol, isopropanol, etc.; polar solvents such as dimethylformamide, dimethyl sulfoxide, hexamethylphosphoric triamide, acetone, acetonitrile, nitromethane and the like. The proportion of the alkylating agent to the compound (5) is normally at least an equimolar amount, preferably in a range from an equimolar amount to 8-time molar amount.

In the following hydrolyzation reaction, any reaction conditions of the normal hydrolyzation can be applied. For example, the hydrolyzation reaction is conducted in a solvent (e.g. water, alcohols such as methanol, ethanol, isopropyl alcohol, etc.; ketones such as acetone, methyl ethyl ketone, etc.; ethers such as dioxane, ethylene glycol dimethyl ether, etc. or a mixed solvent thereof) under the presence of basic compounds such as sodium carbonate, potassium carbonate, sodium hydroxide, potassium hydroxide, barium hydroxide and the like. The reaction is normally conducted at a temperature from room temperature to 200° C., preferably from room temperature to 150° C. Normally, it is completed for about 0.5 to 20 hours.

The compound (2) can also be obtained by hydrolyzing (under the same condition as that of the above hydrolyzation, e.g. a kind of solvent, reaction temperature and reaction time) under the presence of mineral acids such as sulfuric acid, hydrochloric acid, nitric acid, etc.; organic acids such as acetic acid, aromatic sulfonic acid, etc.

Reaction scheme-3

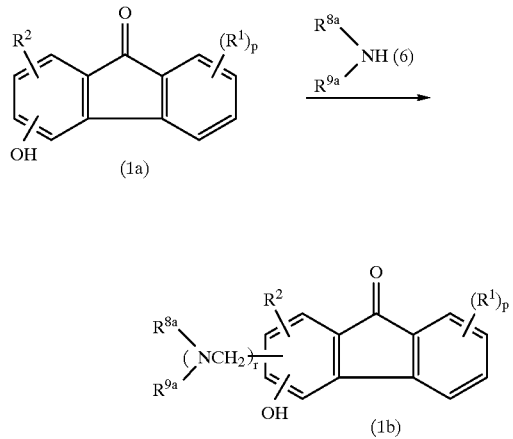

[wherein $R^1$, $R^2$ and p are as defined above; $R^{8a}$ and $R^{9a}$ are the same or different and indicate a hydrogen atom or a lower alkyl group; and r is an integer of 1 to 3; provided that r is 1 or 2 when $R^2$ is a substituent other than a hydrogen atom]

The reaction between the compound (1a) and the compound (6) is referred to as a Mannich reaction and is conducted in a suitable solvent under the presence of formaldehyde and acid or absence of acid. As the solvent, there can be any one which is normally used in the Mannich reaction. Examples thereof include water, alcohols such as methanol, ethanol, isopropanol, etc.; alkane acids such as acetic acid, propionic acid, etc.; acid anhydrides such as acetic anhydride, etc.; polar solvents such as acetone, dimethylformamide, etc; or a mixed solvent thereof. Examples of the acid include mineral acids such as hydrochloric acid, hydrobromic acid, etc.; organic acids such as acetic acid, etc. As the formaldehyde, for example, there can be normally used an aqueous solution, trimer and polymer (paraformaldehyde) containing 20 to 40% by weight of formaldehyde.

The proportion of the compound of the formula (6) to the compound of the formula (1a) is normally at least an equimolar amount, preferably an equimolar amount to 5-time molar amount. The proportion of formaldehyde to the compound of the formula (1a) is normally at least an equimolar amount, preferably in a range from an equimolar amount to 5-time molar amount. The reaction is normally conducted at a temperature from 0 to 200° C., preferably from room temperature to 150° C. Normally, it is completed for about 0.5 to 30 hours.

Reaction scheme-4

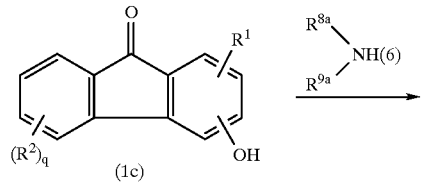

-continued

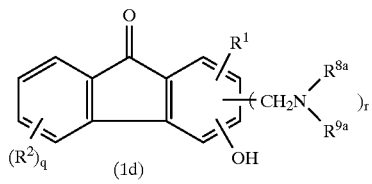

[wherein $R^1$, $R^2$ $R^{8a}$ $R^{9a}$, q and r are as defined above; provided that r is 1 or 2 when $R^1$ is a substituent other than a hydrogen atom].

The reaction between the compound (1c) and the compound (6) can be conducted under the same condition as that between the compound (1a) and the compound (6) according to the above reaction scheme-3.

Reaction scheme-5

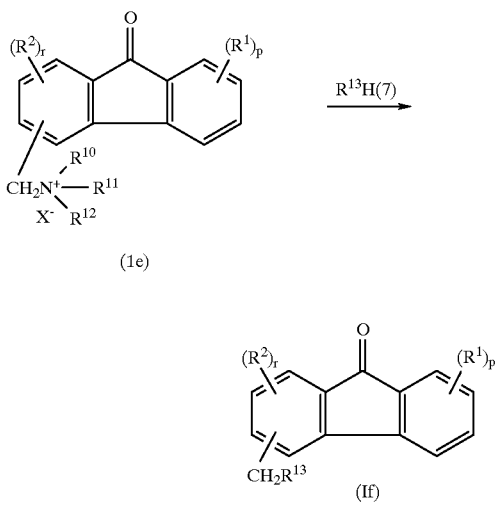

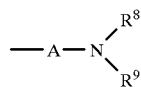
(1f)

[wherein $R^1$, $R^2$, p, r and X are as defined above; $R^{10}$, $R^{11}$ and $R^{12}$ indicate a lower alkyl group; and $R^{13}$ is a group of the formula:

$$-A-N\begin{matrix}R^8\\R^9\end{matrix}$$

($R^8$ and $R^9$ are as defined above), an imidazolyl group or a lower alkoxy group].

The reaction between the compound (1e) and the compound (7) can be conducted in a suitable inert solvent under the presence or absence of basic compounds.

Examples of the inert solvent include aromatic hydrocarbons such as benzene, toluene, xylene, etc.; ethers such as tetrahydrofuran, dioxane, diethylene glycol dimethyl ether, etc.; halogenated hydrocarbons such as dichloromethane, chloroform, carbon tetrachloride, etc.; lower alcohols such as methanol, ethanol, isopropanol, butanol, tert-butanol, etc.; acetic acid, ethyl acetate, acetone, acetonitrile, pyridine, dimethyl sulfoxide, dimethylformamide, hexamethylphosphoric triamide or a mixed solvent thereof.

Examples of the basic compound include carbonates such as sodium carbonate, potassium carbonate, sodium bicarbonate, potassium bicarbonates, etc.; metallic hydroxides such as sodium hydroxide, potassium hydroxide, etc.; metallic alcoholates such as sodium hydride, potassium, sodium, sodium amide, sodium methylate, sodium ethylate, etc.; organic bases such as pyridine, N-ethyldiisopropylamine, dimethylaminopyridine, triethylamine, 1,5-diazocyclo[4.3.0]nonene-5 (DBN), 1,8-diazabicyclo[5.4.0]undecene-7 (DBU), 1,4-diazabicyclo[2.2.2]octane (DABCO) and the like. The proportion of the compound (7) to the compound (1e) is not limited to a specific value, and may vary over a wide range. The proportion of the latter to the former is normally at least an equimolar amount, preferably in a range from an equimolar amount to 15-time molar amount. The reaction is normally conducted at a temperature from about 0 to 200° C., preferably from 0 to 170° C. Normally, it is completed for about 30 minutes to 75 hours.

Reaction scheme-6

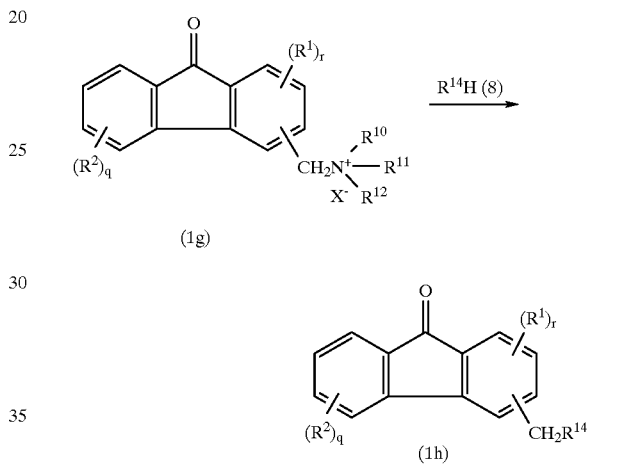

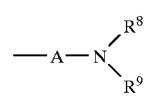
(1h)

[wherein $R^1$, $R^2$, q, r, $R^{10}$, $R^{11}$, $R^{12}$ and X are as defined above; $R^{14}$ is a group of the formula:

$$-A-N\begin{matrix}R^8\\R^9\end{matrix}$$

($R^8$ and $R^9$ are as defined above), an imidazolyl group, a lower alkoxy group or a hydroxyl group-substituted lower alkoxy-lower alkoxy group].

The reaction between the compound (1g) and the compound (8) can be conducted under the same condition as that between the compound (1c) and the compound (7) according to the above reaction scheme-5.

Reaction scheme-7

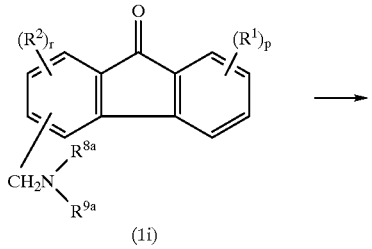
(1i)

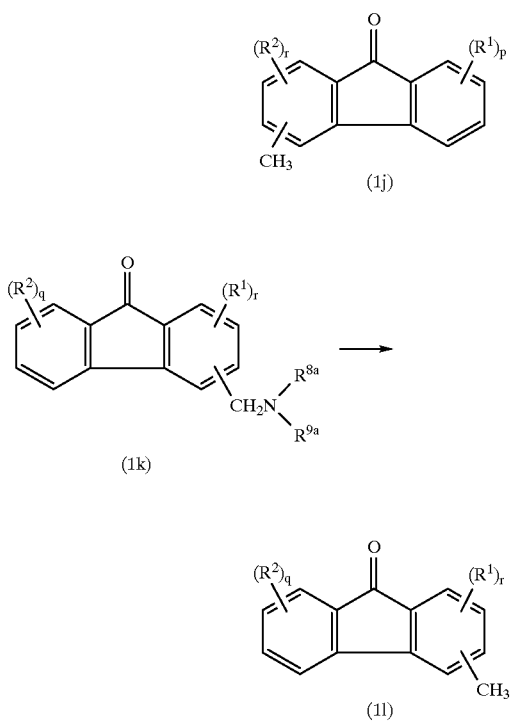

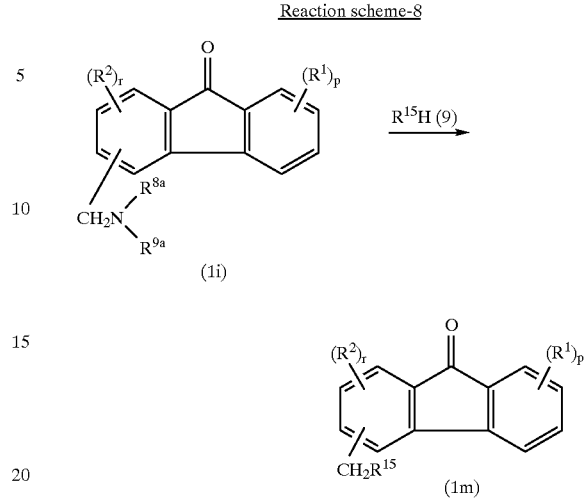

[wherein $R^1$, $R^2$, p, q, r, $R^{8a}$ and $R^{9a}$ are as defined above].

The reaction of introducing the compound (1i) to the compound (1j) and the reaction of introducing the compound (1k) to the compound (1l) are conducted in the presence or absence of a suitable solvent under the presence of catalytic reducing agents and hydrogen donors. Examples of the solvent include water, alcohols such as methanol, ethanol, isopropanol, etc.; organic acids such as formic acid, acetic acid, etc.; esters such as ethyl acetate etc.; ethers such as dioxane, diglyme, tetrahydrofuran, etc.; aromatic hydrocarbons such as benzene, toluene, xylene, etc. or a mixed solvent thereof. Examples of the catalytic reducing agent include palladium black, palladium-carbon, platinum oxide, platinum black, Raney nickel and the like.

Examples of the hydrogen donor include formic acid, ammonium formate, cyclohexene, hydrazine hydrate and the like. The reaction is normally conducted at a temperature from about 0 to 150° C., preferably from 0 to 100° C. Normally, it is completed for about 5 minutes to 12 hours. The amount of the catalytic reducing agent to the compound (1i) or (1k) is normally about 0.01 to 40% by weight, preferably 0.01 to 20% by weight. The proportion of the hydrogen donor to the compound (1i) or (1k) is normally at least an equimolar amount, preferably in a range from an equimolar amount to 10-time molar amount.

[wherein $R^1$, $R^2$, p, r, $R^{8a}$ and $R^{9a}$ are as defined above; and $R^{15}$ is a pyridylthio group, a phenylthio group optionally containing a lower alkoxy group as a substituent on a phenyl ring, a benzimidazolylthio group, an imidazolylthio group or a cycloalkylthio group].

The reaction between the compound (1i) and the compound (9) can be conducted under the same condition as that between the compound (1e) and the compound (7) according to the above reaction scheme-5.

The compound (1) wherein at least one of $R^1$ and $R^2$ is a lower alkoxy group can be introduced to the corresponding compound (1) wherein at least one of $R^1$ and $R^2$ is a hydroxyl group by heating to 30 to 150° C., preferably 50 to 120° C., in a mixture of acids such as hydrobromic acid, hydrochloric acid, etc. and solvents such as acetic acid, etc. The compound wherein at least one of $R^1$ and $R^2$ is a lower alkoxy group can also be introduced to the corresponding compound (1) wherein at least one of $R^1$ and $R^2$ is a hydroxyl group by the hydrolyzation. The hydrolyzation is conducted in a suitable solvent under the presence of acids. Examples of the solvent include ethers such as dioxane, tetrahydrofuran, etc.; halogenated hydrocarbons such as dichloromethane, chloroform, carbon tetrachloride, etc.; aromatic hydrocarbons such as benzene, toluene, xylene, etc.; polar solvents such as acetonitrile, etc.; and a mixed solvent thereof. Examples of the acid include Lewis acids such as boron trioxide, aluminium chloride, boron tribromide, etc.; iodides such as sodium iodide, potassium iodide, etc. or a mixture of Lewis acids and iodides and the like. The reaction is normally conducted at a temperature from room temperature to 150° C., preferably from room temperature to 100° C. Normally, it is completed for about 0.5 to 15 hours.

The compound (1) wherein at least one of $R^1$ and $R^2$ is a lower alkenyloxy group may be produced by reacting the corresponding compound (1) wherein at least one of $R^1$ and $R^2$ is a hydroxyl group with the compound represented by the formula: $R^6X$ (10) (wherein $R^6$ is a lower alkenyl group; and X is as defined above). The reaction is conducted in a suitable solvent under the presence of basic compounds.

Examples of the solvent include water, lower alcohols such as Examples of the solvent include water, lower alcohols such as methanol, ethanol, propanol, etc.; ethers such as diethyl ether, tetrahydrofuran, dioxane, ethylene glycol monomethyl ether, aromatic hydrocarbons such as benzene, toluene, xylene, etc.; esters such as methyl acetate, ethyl acetate, etc.; ketones such as acetone, methyl ethyl ketone, etc.; polar solvents such as acetonitrile, dimethylformamide, dimethyl sulfoxide, hexamethylphosphoric triamide, etc.; or a mixed solvent thereof. Examples of the basic compound include inorganic bases such as sodium hydroxide, potassium hydroxide, sodium carbonate, potassium carbonate, sodium bicarbonate, potassium bicarbonate, sodium hydride, etc.; alkali metals such as metallic sodium, metallic potassium, etc.; alkali metal alcoholates such as sodium ethylate, sodium methylate, etc.; organic bases such as triethylamine, pyridine, N,N-dimetylaniline, N-methylmorpholine, 4-methylaminopyridine, 1,5-diazabicyclo[4.3.0]nonene-5 (DBN), 1,8-diazabicyclo[5.4.0]undecene-7 (DBU), 1,4-diazabicyclo[2.2.2]octane (DABCO) and the like. The proportion of the compound (10) to the compound (1) is normally at least an equimolar amount, preferably in a range from an equimolar amount to 5-time molar amount. The reaction is normally conducted at a temperature from about 0 to 150° C., preferably from room temperature to 100° C. Normally, it is completed for about 0.5 to 20 hours.

The compound (1) wherein at least two of $R^1$ and $R^2$ is a lower alkenyl group and a hydroxyl group may be produced by subjecting the corresponding compound (1) wherein at least one of $R^1$ and $R^2$ is a lower alkenyloxy group to a Claisen rearrangement reaction. The Claisen rearrangement reaction is conducted by heating in a suitable solvent. Examples of the solvent include high boiling point solvents such as dimethylformamide, tetrahydronaphthalene, N,N-dimethylaniline, N,N-diethylaniline, diphenyl ether and the like. The reaction is normally conducted at a temperature from 100 to 250° C., preferably from 150 to 250° C. Normally, it is completed for about 1 to 30 hours.

The compound (1) wherein at least one of $R^1$ and R2 is a lower alkyl group may be produced by reducing the corresponding compound (1) wherein at least one of $R^1$ and $R^2$ is a lower alkenyl group. The reduction reaction is conducted by catalytically reducing in a suitable solvent under the presence of catalysts. Examples of the solvent include alcohols such as water, acetic acid, methanol, ethanol, isopropyl alcohol, etc.; hydrocarbons such as hexane, cyclohexane, etc.; ethers such as diethylene glycol dimethyl ether, dioxane, tetrahydrofuran diethyl ether, etc.; esters such as ethyl acetate, methyl acetate, etc.; polar solvents such as dimethylformamide, etc.; or a mixed solvent thereof. Examples of the catalyst include palladium, palladium black, palladium-carbon, platinum, platinum oxide, copper chromite, Raney nickel and the like. The proportion of the catalyst to the compound (1) is normally in a range from about 0.02- to 1-time molar amount. The reaction temperature is normally about −20 to 100° C., preferably 0 to 70° C., and the hydrogen pressure is preferably 1 to 10 atoms. Normally, the reaction is completed for about 0.5 to 20 hours.

The compound (1) wherein at least one of $R^1$ and/or $R^2$ is a halogen atom may be produced by halogenating the corresponding compound (1) wherein at least one of $R^1$ and $R^2$ is a hydrogen atom. The halogenation reaction is conducted in a suitable solvent under the presence of halogenating agents. Examples of the halogenating agent include halogen molecules such as bromine, chlorine, etc.; N-succinimide halides such as iodine chloride, sulfuryl chloride, N-bromosuccinimide, N-chlorosuccinimide, etc. The proportion of the halogenating agent to the compound (1) is normally in a range from an equimolar amount to 20-time molar amount, preferably from an equimolar amount to 10-time molar amount. Examples of the solvent include halogenated hydrocarbons such as dichloromethane, dichloroethane, chloroform, carbon chloride, etc.; fatty acids such as acetic acid, propionic acid, etc. The reaction is normally conducted at a temperature from about 0° C. to a boiling point of the solvent, preferably from 0 to 50° C. Normally, it is completed for about 0.5 to 20 hours.

In case of the compound (1) wherein at least one of $R^1$ and $R^2$ is a hydroxyl group, the compound (1) can be introduced to the compound (1) wherein at least one of $R^1$ and $R^2$ is a lower alkanoyloxy group by subjecting to lower alkanoylation reaction, using the compound represented by the formula: $(R^7)_2O$ (11) or $R^7X$ (12) (wherein $R^7$ is a lower alkanoyl group; and X is as defined above). The lower alkanoylation reaction is conducted under the presence or absence of basic compounds. Examples of the basic compound include alkali metals such as metallic sodium, metallic potassium, etc. and hydroxides, carbonates or bicarbonates of alkali metals; organic bases such as N,N-dimethylaminopyridine, pyridine, piperidine, etc. The reaction can be conducted in the presence or absence of a solvent. Examples of the solvent include ketones such as acetone, methyl ethyl ketone, etc.; ethers such as diethyl ether, dioxane, etc.; aromatic hydrocarbons such as benzene, toluene, xylene, etc.; water, pyridine and the like. The proportion of the compound (11) or (12) to the starting material is normally at least an equimolar amount, preferably in a range from an equimolar amount to an excessive amount. The reaction is normally conducted at a temperature from about 0 to 200° C., preferably from 0 to 150° C. Normally, the reaction time is about 5 minutes to 5 days.

The objective product thus obtained in each process can be easily separated by a normal separating means, and further purified. Examples of the separating means include solvent extraction, dilution, recrystallization, column chromatography, preparative thin-layer chromatography and the like.

In the fluorenone derivatives represented by formula (1), compound having ammonium group may be easily reacted with halogen anion(such as chlorine anion, bromine anion, iodine anion, etc.) to form a salt.

As a matter of course, the compound of the present invention includes stereoisomers and optical isomers.

The compound of the present invention may be normally used in the form of a general pharmaceutical composition. The pharmaceutical composition may be prepared using diluents or excipients such as filler, extender, binder, humidifying agent, disintegrator, surfactant, lubricant and the like which may be normally used. According to the curing purpose, the pharmaceutical composition may be made in any forms such as tablet, pill, powder, liquid preparation, suspension, emulsion, granule, capsule, suppository, injection (e.g. liquid preparation, suspension, etc.), ointment and the like. When molding the pharmaceutical composition in the form of tablet, there can be widely used any carriers conventionally used in this field. Examples of the carrier include excipients such as lactose, white sugar, sodium chloride, glucose, urea, starch, calcium carbonate, kaoline, crystal cellulose, silica, etc.; binders such as water, ethanol, propanol, simple syrup, glucose liquid, starch liquid, gelatin solution, carboxymethyl cellulose, shellac, methyl cellulose, potassium phosphate, polyvinyl pyrrolidone, etc.; disintegrators such as dry starch, sodium alginate, agar powder, laminaria powder, sodium bicarbonate, calcium carbonate, polyoxyethylene sorbitan fatty esters, sodium lauryl sulfate, monoglyceride stearate, starch, lactose, etc.; disintegration restraining agents such as white sugar, stearin, cacao butter, hydrogenated oil, etc.; absorption accelerating agents such as quaternary ammonium base, sodium lauryl sulfate, etc.; humectants such as glycerin, starch, etc.; absorbents such as starch, lactose, kaoline, bentonite, colloidal silicic acid, etc.; lubricants such as purified talc, salt stearate, boric acid powder, polyethylene glycol, etc. If necessary, tablets may be coated with a normal film to prepare sugar-coated tablets, gelatin-coated tablets, enteric-coated tablets, film-coated tablets or tablets comprising two or more layers. When molding the pharmaceutical composition in the form of pill, there can be widely used any carriers known in this field. Examples of the carrier include excipients such as glucose, lactose, starch, cacao butter, hydrogenated vegetable oil, kaoline, talc, etc.; binders such as powdered acacia gum, powdered traganth, gelatin, ethanol, etc; and disintegrators such as laminaria, agar, etc. When molding the pharmaceutical preparation in the form of suppository, there can be widely used any known carriers. Example of the carrier include esters such as polyethylene glycol, cacao butter, higher alcohol, etc.; gelatin and semisynthetic glyceride. When preparing the pharmaceutical composition in the form of injection, the resulting solution, emulsion and suspension are preferably sterilized and made isotonic with respect to the blood. When preparing the pharmaceutical composition in the form of solution, emulsion and suspension, there can be used any diluents generally used in this field. Examples of the diluent include water, aqueous lactose, ethyl alcohol, propylene glycol, ethoxylated isostearyl alcohol, polyoxylated isostearyl alcohol, polyoxyethylene sorbitan fatty esters and the like. The pharmaceutical composition may contain salt, glucose or glycerin in an amount sufficient to prepare an isotonic solution. There can also be added solubilizers, buffer agents, pain-alleviating agents and the like. If necessary, the pharmaceutical composition may contain colorants, preservatives, perfumes, flavors, sweeteners, other pharmaceutical products and the like. When molding the pharmaceutical composition in the form of paste, cream or gel, there can be widely used known diluents. Example of the diluent include white soft paraffine, paraffine, glycerin, cellulose derivative, polyethylene glycol, silicon, bentonite and the like.

The amount of the compound of the formula (1) or a salt thereof to be formulated in the pharmaceutical composition is not limited to a specific one but may be vary over a wide range. It is preferably 1 to 70% by weight based on the weight of the pharmaceutical composition.

The administration method of the above pharmaceutical composition is not specifically limited and can be selected according to the form of the preparation, patient's age and gender, other conditions, symptoms of diseases and the like. For example, the pills, liquids, suspensions, emulsions, granules and capsules are orally administered. The injections are intravenously administered either alone or together with ordinary auxiliary agents such as glucose, amino acid and the like. Further, the injections may be singly administered intramuscularly, intracutaneously, subcutaneously or intraperitoneally, if necessary. The suppository is administered intrarectally.

The dosage of the pharmaceutical composition is suitably selected according to the purpose of use, patient's age and gender, symptoms of diseases and the like. Normally, it is preferred that the compound of the formula (1) or a salt thereof as the active component is administered per day with a dairy dose of about 0.2 to 200 mg/kg.

The following Preparation Examples, Reference Examples, Examples and Pharmacological tests further illustrate the present invention in detail but are not to be construed to limit the scope thereof.

| Preparation Example 1 | | |
|---|---:|---|
| 1,6-Diallyl-2,7-dihydroxyfluorenone | 5 | mg |
| Starch | 132 | mg |
| Magnesium stearate | 18 | mg |
| Lactose | 45 | mg |
| Total | 200 | mg |

According to a normal method, a tablet of the above composition was produced.

| Preparation Example 2 | | |
|---|---:|---|
| 1,6-Diallyl-2,5-dihydroxyfluorenone | 150 | mg |
| Avicel (tradename, manufactured by Asahi Kasei Co., Ltd.) | 40 | g |
| Cornstarch | 30 | g |
| Magnesium stearate | 2 | g |
| Hydroxypropyl methyl cellulose | 10 | g |
| Polyethylene glycol 6000 | 3 | g |
| Castor oil | 40 | g |
| Methanol | 40 | g |

The compound of the present invention, Avicel, cornstarch and magnesium stearate are mixed and abraded, and the mixture is compressed by a punch with a sugar-coat R (10 mm). The resulting tablets are coated with a film-coating agent comprising hydroxypropyl methyl cellulose, polyethylene glycol 6000, castor oil and methanol to produce film-coated tablets.

REFERENCE EXAMPLE 1

In tetrahydrofuran (100 ml), magnesium (1.3 g) was reacted with 4-bromoveratrole (13 g) to prepare a Grignard reagent. While cooling in an ice-water bath, a solution of 2-(2,4,5-trimethoxyphenyl)-4,4-dimethyl-2-oxazoline (7.7 g) in tetrahydrofuran (100 ml) was added thereto. After stirring at room temperature for 48 hours, an aqueous saturated ammonium chloride solution (150 ml) was added and stirred for 15 minutes. Then, the mixed solution was separated to extract the aqueous layer with tetrahydrofuran (150 ml). The organic layers were combined each other and concentrated by an evaporator. The residue was dissolved in 10% hydrochloric acid (100 ml), which was washed with diethyl ether. The aqueous layer was cooled in an ice-water bath, then neutralized by adding a 20% aqueous sodium hydroxide solution. It was extracted with ethyl acetate, washed with a saturated saline solution and then dried over sodium sulfate. The solvent was distilled off to give 10 g of 2-[2-(3,4-dimethoxyphenyl)-4,5-dimethoxyphenyl]-4,4-dimethyl-2-oxazoline as a pale brown oil.

$^1$H-NMR (CDCl$_3$)δ ppm; 1.31 (6H, s), 3.79 (2H, s), 3.89 (3H, s), 3.92 (6H, s), 3.92 (3H, s), 6.83 (1H, s), 6.88–6.96 (3H, m), 7.25 (1H, s)

REFERENCE EXAMPLE 2

2-[2-(3,4-Dimethoxyphenyl)-4,5-dimethoxyphenyl]-4,4-dimethyl-2-oxazoline (10 g) was dissolved in nitromethane (100 ml), to which was added methyl iodide (10 ml), and the mixture was allowed to stand at room temperature for 24 hours. It was concentrated by an evaporator, and methanol (150 ml) and a 20% aqueous sodium hydroxide solution (150 ml) were added to the residue to reflux for 18 hours. The solvent was distilled off until the system becomes ununiform, and water was added until it becomes transparent. After washing with diethyl ether (200 ml), the aqueous layer was cooled in a ice-water bath and concentrated hydrochloric acid was added until it becomes acidic. The insoluble matter formed was filtered, washed with water and dried to give 7.7 g of 2-(3,4-dimethoxyphenyl)-4,5-dimethoxybenzoic acid as a white powder.

By using a suitable starting material, compounds shown in Table 1 were obtained according to the same manner as that described in Reference Example 1.

COMPOUND OF REFERENCE EXAMPLE 4

$^1$H-NMR (CDCl$_3$, δ ppm); 1.29 (6H, s), 3.81 (2H, s), 3.83 (3H, s), 6.88 (1H, dd, J=1 Hz, J=5.5 Hz), 6.90–7.01 (2H, m), 7.29–7.70 (4H, m), 7.72 (1H, dd, J=1 Hz, J=6.5 Hz).

COMPOUND OF REFERENCE EXAMPLE 5

1H-NMR (CDCl$_3$, δ ppm); 1.25 (6H, s), 3.73 (3H, s), 3.75 (2H, s), 6.89 (1H, d, J=8 Hz), 7.00 (1H, ddd, J=1 Hz, J=7.5 Hz, J=7.5 Hz), 7.24 (1H, dd, J=1.5 Hz, J=7.5 Hz), 7.28–7.39 (3H, m), 7.47 (1H, ddd, J=1.5 Hz, J=7.5 Hz, J=7.5 Hz), 7.84 (1H, dd, J=1.5 Hz, J=7.5 Hz).

COMPOUND OF REFERENCE EXAMPLE 6

$^1$H-NMR (CDCl$_3$, δ ppm); 1.31 (6H, s), 3.82 (2H, s), 3.84 (3H, s), 6.89–6.95 (2H, m), 7.29–7.30 (4H, m), 7.46 (1H, ddd, J=1.5 Hz, J=7.5 Hz, J=7.5 Hz), 7.70 (1H, dd, J=1.5 Hz, J=7.5 Hz).

TABLE 1

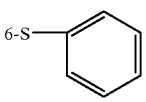

| Reference Example | $(R^1)_p$ | $(R^2)_q$ | $R^4$ | $R^5$ | Physical properties |
|---|---|---|---|---|---|
| 3 | 4-OCH$_3$ | 6-S-phenyl | CH$_3$ | CH$_3$ | colorless prism-like crystals (n-hexane-ethyl acetate) mp. 89.0–90.0° C. |
| 4 | 3-OCH$_3$ | H | CH$_3$ | CH$_3$ | pale yellow oily |
| 5 | 2-OCH$_3$ | H | CH$_3$ | CH$_3$ | colorless oily |
| 6 | 4-OCH$_3$ | H | CH$_3$ | CH$_3$ | pale yellow oily |
| 7 | 3-SCH$_3$ 6-OCH$_3$ | H | CH$_3$ | CH$_3$ | pale yellow oily |
| 8 | 4-OCH$_3$ | 4-OCH$_3$ | CH$_3$ | CH$_3$ | pale yellow oily |
| 9 | 4-OCH$_3$ | 5-OCH$_3$ | CH$_3$ | CH$_3$ | colorless prism-like crystals (n-hexane-diethyl ether) mp. 65.0–66.0° C. |
| 10 | 4-OCH$_3$ | 6-OCH$_3$ | CH$_3$ | CH$_3$ | colorless needle-like crystals (n-hexane-diethyl ether) mp. 83.5–84.5° C. |
| 11 | 4-OCH$_3$ | 3-OCH$_3$ | CH$_3$ | CH$_3$ | colorless prism-like crystals (n-hexane) mp. 69.0–70.0° C. |
| 12 | H | 3-OCH$_3$ | CH$_3$ | CH$_3$ | colorless prism-like crystals (n-hexane-diethyl ether) mp. 67.0–68.0° C. |
| 13 | 3-OCH$_3$ 4-OCH$_3$ | H | CH$_3$ | CH$_3$ | pale yellow oily |
| 14 | 4-OCH(CH$_3$)$_2$ | 3-OCH$_3$ | CH$_3$ | CH$_3$ | pale yellow oily |
| 15 | 3-OCH$_3$ 4-OCH$_3$ | 3-OCH$_3$ | CH$_3$ | CH$_3$ | pale yellow oily |
| 16 | 4-OCH$_3$ | 4-OCH$_3$ 5-OCH$_3$ | CH$_3$ | CH$_3$ | pale yellow oily |

COMPOUND OF REFERENCE EXAMPLE 7

¹H-NMR (CDCl₃, δ ppm); 1.26 (6H, s), 3.46 (3H, s), 3.72 (3H, s), 3.77 (2H, s), 6.84 (1H, d, J=8.5 Hz), 7.20–7.40 (4H, m), 7.48 (1H, ddd, J=1.5 Hz, J=7.5 Hz, J=7.5 Hz), 7.84 (1H, dd, J=1.5 Hz, J=7.5 Hz).

COMPOUND OF REFERENCE EXAMPLE 8

¹H-NMR (CDCl₃, δ ppm); 1.29 (6H, s), 3.79 (2H, s), 3.85 (6H, s), 6.83–6.95 (4H, m), 7.29–7.35 (2H, m), 7.65–7.69 (1H, m).

COMPOUND OF REFERENCE EXAMPLE 8

¹H-NMR (CDCl₃, δ ppm); 1.29 (6H, s), 3.79 (2H, s), 3.85 (6H, s), 6.83–6.95 (4H, m), 7.29–7.35 (2H, m), 7.65–7.69 (1H, m).

COMPOUND OF REFERENCE EXAMPLE 13

¹H-NMR (CDCl₃, δ ppm); 1.30 (6H, s), 3.83 (2H, s), 3.89 (3H, s), 3.92 (3H, s), 6.88–6.99 (3H, m), 7.31–7.51 (3H, m), 7.69–7.74 (1H, m).

COMPOUND OF REFERENCE EXAMPLE 14

¹H-NMR (CDCl₃, δ ppm); 1.22 (6H, s), 1.36 (6H, d, J=6 Hz), 3.72 (2H, s), 3.76 (3H, s), 4.58 (1H, sept, J=6 Hz), 6.85–6.92 (2H, m), 7.03 (1H, dd, J=2 Hz, J=7.5 Hz), 7.20–7.34 (4H, m).

COMPOUND OF REFERENCE EXAMPLE 15

¹H-NMR (CDCl₃, δ ppm); 1.22 (6H, s), 3.71 (2H, s), 3.78 (3H, s), 3.86 (3H, s), 3.89 (3H, s), 6.87–6.91 (3H, m), 7.04 (1H, dd, J=2.5 Hz, J=9.0 Hz), 7.27–7.36 (2H, m).

COMPOUND OF REFERENCE EXAMPLE 16

¹H-NMR (CDCl₃, δ ppm); 1.31 (6H, s), 3.79 (2H, s), 3.85 (3H, s), 3.91 (3H, s), 3.95 (3H, s), 6.82 (1H, s), 6.90 (2H, d, J=9.0 Hz), 7.24 (1H, s), 7.30 (2H, d, J=9.0 Hz).

By using a suitable starting material, compounds shown in Tables 2 were obtained according to the same manner as that described in Reference Example 2.

TABLE 2

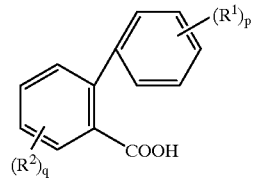

| Reference Example | $(R^1)_p$ | $(R^2)_q$ | Physical properties |
|---|---|---|---|
| 17 | 4-OCH₃ | 3-OCH₃ | colorless needle-like crystals (chloroform) mp. 171.0–173.0° C. |
| 18 | 4-OCH₃ | 5-OCH₃ | colorless prism-like crystals (ethanol) mp. 153.0–155.0° C. |
| 19 | 4-OCH₃ | 4-OCH₃ | colorless particulate crystals (ethanol) mp. 169.0–172.0° C. |
| 20 | 3-OCH₃ 4-OCH₃ | H | colorless prism-like crystals (ethyl acetate) mp. 165.0–167.0° C. |
| 21 | H | 3-OCH₃ | colorless prism-like crystals (ethyl acetate) mp. 177.0–179.0° C. |

TABLE 2-continued

| Reference Example | $(R^1)_p$ | $(R^2)_q$ | Physical properties |
|---|---|---|---|
| 22 | 4-OCH₃ | 6-OCH₃ | |
| 23 | 4-OCH(CH₃)₂ | 3-OCH₃ | colorless powdered mp. 126–127.0° C. |
| 24 | 2-OCH₃ | H | colorless powdered (n-hexane-ethyl acetate) mp. 150.0–152.0° C. |
| 25 | 3-OCH₃ | H | brown oil |
| 26 | 4-OCH₃ | H | colorless powdered crystals mp. 143.0–145.0° C. (decomposed) |
| 27 | 3-OCH₃ 4-OCH₃ | 3-OCH₃ | white powdered |
| 28 | 4-OCH₃ | 4-OCH₃ 5-OCH₃ | pale brown powdered mp. 194.0–195.0° C. |

COMPOUND OF REFERENCE EXAMPLE 25

¹H-NMR (CDCl₃, δ ppm); 3.80 (3H, s), 6.87–6.93 (3H, m), 7.24–7.58 (3H, m), 7.54 (1H, ddd, J=1.5 Hz, J=7.5 Hz, J=7.5 Hz), 7.92 (1H, dd, J=1.5 Hz, J=7.5 Hz), 9.83 (1H, s).

By using a suitable starting material, the following compound was obtained according to the same manner as that described in Reference Example 1.

TABLE 3

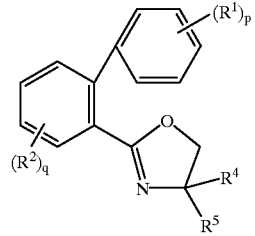

| Reference Example | $(R^1)_p$ | $(R^2)_q$ | $R^4$ | $R^5$ | Physical properties |
|---|---|---|---|---|---|
| 29 | 3-CH(CH₃)₂ 5-CH(CH₃)₂ 4-OCH₃ | 3-OCH₃ | CH₃ | CH₃ | ¹H-NMR (CDCl₃, δ ppm); 1.14(6H, s), 1.23(6H, d, J=2.3Hz), 1.25(6H, d, J=2.6Hz), 3.28–3.39(2H, m), 3.75(3H, s), 3.77(3H, s), 7.00–7.05(3H, m), 7.25–7.35(2H, m) |

EXAMPLE 1

Polyphosphoric acid which had been newly prepared from diphosphorus pentaoxide (50 g) and phosphoric acid (50 ml)

was heated at 100° C. With stirring, 2-(3,4-dimethoxyphenyl)-4,5-dimethoxybenzoic acid (7.5 g) was added thereto as it is (in the crystal form) in several portions. After stirring at 100 to 120° C. for 2 hours, the reaction solution was poured into water (1.5 liter) and extracted with chloroform. The extract was washed with 2% aqueous sodium hydroxide solution, water and a saturated saline solution, then dried over sodium sulfate. The solvent was distilled off, and the residue was purified by silica gel column chromatography (eluent: chloroform) and recrystallized from ethyl acetate-n-hexane to give 5.0 g of 2,3,6,7-tetramethoxyfluorenone as an orange needle-like crystal.

Melting point: 194.0–195.0° C.

EXAMPLE 2

To a mixed solution of acetic acid (20 ml) and 47% hydrobromic acid (10 ml), 2,3,6,7-tetramethoxyfluorenone (8.0 g) was added and the mixture was refluxed for 15 hours. After cooling, the precipitated crystals were filtered, washed with water and then recrystallized from water-containing ethanol to give 5.0 g of 2,3,6,7-tetrahydroxyfluorenone as a claret powder.

Melting point: more than 300° C.

$^1$H-NMR (DMSO-$d_6$) δ ppm; 6.83 (4H, s), 9.33 (2H, bs), 9.79 (2H, bs)

By using a suitable starting material, compounds of the Examples 9 to 24, 26 to 65, 68, 69, 81, 86, 89, 91, 105, 109, 110, 112 to 133, 135 to 147 and 152 were obtained according to the same manner as that described in Example 2.

EXAMPLE 3

2,3-Dimethoxyfluorenone (15 g) was dissolved in toluene (300 ml), to which was added anhydrous aluminum chloride (20 g) and the mixture was stirred at 90° C. for 2 hours. After cooling, the reaction solution was poured into ice water (1.5 liter). Then, the insoluble matter formed was filtered, washed with water, dried and recrystallized from ethyl acetate to give 9.8 g of 2,3-dihydroxyfluorenone as a yellow needle-like crystal.

Melting point: 247.0–248.0° C.

By using a suitable starting material, compounds of the Examples 9 to 19, 21 to 65, 68, 69, 81, 86, 89, 91, 105, 109, 110, 112 to 133, 135 to 147 and 152 were obtained according to the same manner as that described in Example 3.

EXAMPLE 4

To dimethylformamide (200 ml), 2,3-dihydroxyfluorenone (9.8 g) and potassium carbonate (15 g) were added and the mixture was stirred at room temperature for 30 minutes. To this was added allyl bromide (10 ml), followed by stirring at room temperature for 15 hours. The solvent was distilled off by an evaporator and water was added to the residue, which was extracted with ethyl acetate. The extract was washed with water and a saturated saline solution, and then dried over sodium sulfate. The solvent was distilled off and the residue was recrystallized from ethanol to give 11.5 g of 2,3-diallyloxyfluorenone as a yellow needle-like crystal.

Melting point: 112.0–113.0° C.

By using a suitable starting material, compounds of the Examples 55, 57, 67, 70 to 73, 75 to 77, 88, 90, 92 to 95, 98, 102, 103, 104 and 148 to 150 were obtained according to the same manner as that described in Example 4.

EXAMPLE 5

2,3-Diallyloxyfluorenone (11.5 g) was added to tetralin (100 ml) and the mixture was heated at reflux for 2 hours. After cooling, the reaction solution was purified by silica gel column chromatography (eluent: n-hexane/ethyl acetate (9:1)) and recrystallized from toluene to give 5.5 g of 1,4-diallyl-2,3-dihydroxyfluorenone as a red needle-like crystal.

Melting point: 153.0–154.0° C.

By using a suitable starting material, compounds of the Examples 9 to 12, 14 to 19, 22, 27 to 37, 41 to 45, 47 to 62, 64, 68 and 91 were obtained according to the same manner as that described in Example 5.

EXAMPLE 6

To ethanol (30 ml), 1,4-diallyl-2,3-dihydroxyfluorenone (1.0 g) and 5% palladium-carbon (0.1 g) were added, and the mixture was catalytically reduced at normal temperature, at normal pressure. After the catalyst was removed, the reaction product was concentrated and recrystallized from water-containing ethanol to give 0.5 g of 1,4-di-n-propyl-2,3-dihydroxyfluorenone as a red needle-like crystal.

Melting point: 193.0–194.0° C.

By using a suitable starting material, compounds of the Examples 12, 32, 36 to 39, 51 to 54, 109, 110, 114, 117, 122, 124, 126 to 134, 139, 143, 145 to 147 and 153 were obtained according to the same manner as that described in Example 6

EXAMPLE 7

1,5-Di-n-propyl-2,7-dihydroxyfluorenone (0.5 g) was suspended in acetic acid (5 ml), to which was added sulfuryl chloride (1.0 ml) and the mixture was stirred at room temperature for 15 hours. Water (20 ml) was added to the reaction solution and the resulting precipitate was filtered. The precipitate was washed with water, dried and then purified by silica gel column chromatography (eluent: dichloromethane). It was recrystallized from chloroform-n-hexane to give 0.3 g of 3,8-dichloro-1,6-di-n-propyl-2,7-dihydroxyfluorenone as an orange powder.

Melting point: 134.5–135.5° C.

By using a suitable starting material, compounds of the Examples 33, 34, 65, 89 to 92, 113 and 148 to 150 were obtained according to the same manner as that described in Example 7.

EXAMPLE 8

1,6-Diallyl-2,7-dihydroxyfluorenone (1.0 g) was dissolved in pyridine (10 ml), to which was added acetic anhydride (1.0 ml) and the mixture was stirred at room temperature for 15 minutes. Water (200 ml) was added to the reaction solution and the resulting precipitate was filtered. The precipitate was washed with water, dried and then purified by silica gel column chromatography (eluent: dichloromethane). It was recrystallized from dichloromethane-n-hexane to give 1.2 g of 1,6-diallyl-2,7-diacetoxyfluorenone as a yellow needle-like crystal.

Melting point: 170.0–172.0° C.

By using a suitable starting material, compounds of the Examples 107, 108, 111 and 134 were obtained according to the same manner as that described in Example 8.

By using a suitable starting material, compounds shown in the Table 4 were obtained according to the same manner as that described in Example 1.

TABLE 4

Structure: fluoren-9-one with $(R^2)_q$ on one ring and $(R^1)_p$ on the other.

| Example | $(R^1)_p$ | $(R^2)_q$ | Shape of crystals (Solvent for recrystallization) | Melting point (° C.) |
|---|---|---|---|---|
| 9 | 1-OH<br>2-CH$_2$CH=CH$_2$ | H | yellow prism-like crystals<br>(ethanol) | 90.9–92.0 |
| 10 | 1-OH<br>4-CH$_2$CH=CH$_2$ | H | yellow prism-like crystals<br>(n-hexane) | 41.0–42.0 |
| 11 | 1-OH<br>2-CH$_2$CH=CH$_2$<br>4-CH$_3$ | H | yellow powdered<br>(n-hexane) | 92.0–96.0 |
| 12 | 1-OH<br>2-CH$_2$CH$_2$CH$_3$<br>4-CH$_3$ | H | yellow powdered<br>(n-hexane) | 109.0–111.0 |
| 13 | 1-OH | 7-OH | yellow powdered | 193.0–194.0 |
| 14 | 1-OH<br>2-CH$_2$CH=CH$_2$ | 6-CH$_2$CH=CH$_2$<br>7-OH | orange powdered<br>(chloroform-n-hexane) | 165.0–167.0 |
| 15 | 1-OH<br>4-CH$_2$CH=CH$_2$ | 6-CH$_2$CH=CH$_2$<br>7-OH | orange powdered<br>(chloroform-n-hexane) | 176.0–177.0 |
| 16 | 1-OH<br>2-CH$_2$CH=CH$_2$<br>4-CH$_2$CH=CH$_2$ | 6-CH$_2$CH=CH$_2$<br>7-OH<br>8-CH$_2$CH=CH$_2$ | yellow powdered<br>(n-hexane) | 83.0–86.0 |
| 17 | 1-CH$_2$CH=CH$_2$<br>2-OH | H | orange needle-like crystals<br>(chloroform-n-hexane) | 166.0–168.0 |
| 18 | 2-OH<br>3-CH$_2$CH=CH$_2$ | H | orange needle-like crystals<br>(chloroform-n-hexane) | 153.0–154.0 |
| 19 | 1-CH$_2$CH=CH$_2$<br>2-OH<br>3-CH$_2$CH=CH$_2$ | H | orange needle-like crystals<br>(n-hexane) | 138.0–141.0 |
| 20 | 2-OH<br>3-OH | H | Yellow powdered<br>(ethyl acetate) | 247.0–248.0 |
| 21 | 1-CH$_2$CH=CH<br>2-OH<br>3-OH<br>4-CH$_2$CH=CH$_2$ | H | red needle-like crystals<br>(toluene) | 153.0–154.0 |
| 22 | 1-CH$_2$CH$_2$CH$_3$<br>2-OH<br>3-OH<br>4-CH$_2$CH$_2$CH$_3$ | H | red needle-like crystals<br>(water-containing ethanol) | 193.0–194.0 |
| 23 | 2-OH<br>3-OH | 5-OH | red needle-like crystals<br>(water-containing ethanol) | more than 300 |
| 24 | 2-OH<br>3-OH | 7-OH | dark orange needle-like crystals<br>(water-containing ethanol) | more than 300 |
| 25 | 2-OH<br>3-OH | 6-OH<br>7-OH | claret powdered<br>(water-containing ethanol) | more than 300 |
| 26 | 2-OH | 5-OH | red powdered<br>(ethanol) | more than 300 |
| 27 | 1-CH$_2$CH=CH$_2$<br>2-OH | 5-OH<br>6-CH$_2$CH=CH$_2$ | orange powdered<br>(diethyl ether-n-hexane) | 182.0–185.0 |
| 28 | 1-CH$_2$CH=CH$_2$<br>2-OH | 5-OH<br>8-CH$_2$CH=CH$_2$ | orange powdered<br>(diethyl ether-n-hexane) | 160.0–164.0 |
| 29 | 2-OH<br>3-CH$_2$CH=CH$_2$ | 5-OH<br>6-CH$_2$CH=CH$_2$ | violet powdered<br>(chloroform-diethyl ether) | 183.0–185.0 |
| 30 | 2-OH<br>3-CH$_2$CH=CH$_2$ | 5-OH<br>8-CH$_2$CH=CH$_2$ | orange powdered<br>(chloroform-diethyl ether) | 193.0–196.0 |
| 31 | 1-CH$_2$CH=CH$_2$<br>2-OH<br>3-CH$_2$CH=CH$_2$ | 5-OH<br>6-CH$_2$CH=CH$_2$<br>8-CH$_2$CH=CH$_2$ | red powdered<br>(diethyl ether-n-hexane) | 91.0–93.0 |
| 32 | 1-CH$_2$CH$_2$CH$_3$<br>2-OH<br>3-CH$_2$CH$_2$CH$_3$ | 5-OH<br>6-CH$_2$CH$_2$CH$_3$<br>8-CH$_2$CH$_2$CH$_3$ | red prism-like crystals<br>(n-hexane) | 113.0–114.0* |
| 33 | 1-CH$_2$CH=CH$_2$<br>2-OH<br>3-Cl | 5-OH<br>6-CH$_2$CH=CH$_2$<br>8-Cl | orange powdered<br>(chloroform-n-hexane) | 154.0–156.0 |
| 34 | 1-CH$_2$CH=CH$_2$<br>2-OH<br>3-Cl | 5-OH<br>6-Cl<br>8-CH$_2$CH=CH$_2$ | orange powdered<br>(chloroform-n-hexane) | 158.0–160.0 |
| 35 | 2-OH<br>3-CH$_2$CH$_2$=CH$_2$ | 5-OH | red needle-like crystals<br>(chloroform-methanol) | 235.0–237.0 |
| 36 | 2-OH<br>3-CH(CH$_3$)$_2$ | 5-OCH$_3$ | red powdered<br>(ethyl acetate-n-hexane) | 214.0–217.0 |

TABLE 4-continued

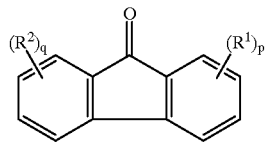

| Example | (R¹)p | (R²)q | Shape of crystals (Solvent for recrystallization) | Melting point (° C.) |
|---|---|---|---|---|
| 37 | 2-OH<br>3-CH(CH₃)₂ | 5-OCH₃<br>7-CH(CH₃)₂ | orange powdered<br>(n-hexane) | 243.0–245.0 |
| 38 | 1-CH(CH₃)CH₃<br>2-OH<br>3-CH(CH₃)CH₃ | 5-OCH₃ | red powdered<br>(ethyl acetate-n-hexane) | 192.0–194.0 |
| 39 | 2-OH<br>3-CH(CH₃)CH₃ | 5-OCH₃<br>8-CH(CH₃)CH₃ | red powdered<br>(ethyl acetate-n-hexane) | 224.0–226.0 |
| 40 | 2-OH | 6-OH | dark orange powdered<br>(ethyl acetate) | 268.0–271.0 |
| 41 | 1-CH₂CH=CH₂<br>2-OH | 5-CH₂CH=CH₂<br>6-OH | yellow powdered<br>(chloroform-diethyl ether-n-hexane) | 201.0–204.0 |
| 42 | 1-CH₂CH=CH₂<br>2-OH | 6-OH<br>7-CH₂CH=CH₂ | orange powdered<br>(ethyl acetate-n-hexane) | 206.0–209.0 |
| 43 | 2-OH<br>3-CH₂CH=CH₂ | 5-CH₂CH=CH₂<br>6-OH | orange powdered<br>(chloroform-diethyl ether n-hexane) | 230.0–233.0 |
| 44 | 2-OH<br>3-CH₂CH=CH₂ | 6-OH<br>7-CH₂CH=CH₂ | orange powdered<br>(chloroform-methanol) | 225.0–228.0 |
| 45 | 1-CH₂CH=CH₂<br>2-OH<br>3-CH₂CH=CH₂ | 5-CH₂CH=CH₂<br>6-OH<br>7-CH₂CH=CH₂ | yellow powdered<br>(n-hexane) | 143.0–145.0 |
| 46 | 2-OH | 7-OH | violet powdered<br>(ethyl acetate) | more than 300 |
| 47 | 1-CH₂CH=CH₂<br>2-OH | 6-CH₂CH=CH₂<br>7-OH | orange powdered<br>(ethyl acetate-n-hexane) | 185.0–188.0 |
| 48 | 1-CH₂CH=CH₂<br>2-OH | 7-OH<br>8-CH₂CH=CH₂ | red powdered<br>(chloroform) | 143.0–145.0 |
| 49 | 2-OH<br>3-CH₂CH=CH₂ | 6-CH₂CH=CH₂<br>7-OH | beige powdered<br>(ethyl acetate-n-hexane) | 189.0–193.0 |
| 50 | 1-CH₂CH=CH₂<br>2-OH<br>3-CH₂CH=CH₂ | 6-CH₂CH=CH₂<br>7-OH<br>8-CH₂CH=CH₂ | red needle-like crystals<br>(n-hexane) | 90.0–91.0 |
| 51 | 1-CH₂CH₂CH₃<br>2-OH | 6-CH₂CH₂CH₃<br>7-OH | reddish orange needle-like crystals<br>(water-containing ethanol) | 192.0–193.0 |
| 52 | 2-OH<br>3-CH₂CH₂CH₃ | 6-CH₂CH₂CH₃<br>7-OH | orange needle-like crystals<br>(water-containing ethanol) | 213.0–214.0 |
| 53 | 1-CH₂CH₂CH₃<br>2-OH<br>3-CH₂CH₂CH₃ | 6-CH₂CH₂CH₃<br>7-OH<br>8-CH₂CH₂CH₃ | yellow needle-like crystals<br>(n-hexane) | 88.0–89.0 |
| 54 | 1-CH₂CH₂CH₃<br>2-OH<br>3-Cl | 6-CH₂CH₂CH₃<br>7-OH<br>8-Cl | orange powdered<br>(chloroform-n-hexane) | 134.5–135.5 |
| 55 | 1-CH₂CH=CH₂<br>2-OH<br>3-CH₂CH=CH₂ | 6-CH₂CH=CH₂<br>7-OCH₂CH=CH₂ | orange needle-like crystals<br>(chloroform-n-hexane) | 164.0–165.0 |
| 56 | 1-CH₂CH=CH₂<br>2-OH<br>3-OH<br>4-CH₂CH=CH₂ | 6-CH₂CH=CH₂<br>7-OH | dark orange prism-like crystals<br>(toluene) | 143.0–145.0 |
| 57 | 1-CH₂CH=CH₂<br>2-OH<br>3-OH<br>4-CH₂CH=CH₂ | 7-OCH₂CH₂=CH₂ | orange powdered<br>(chloroform-n-hexane) | 165.0–167.0 |
| 58 | 2-CH₂CH=CH₂ | H | orange powdered | 176.0–177.0 |

TABLE 4-continued

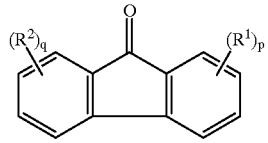

| Example | (R¹)ₚ | (R²)_q | Shape of crystals (Solvent for recrystallization) | Melting point (° C.) |
|---|---|---|---|---|
|  | 3-OH |  | (chloroform) |  |
| 59 | 3-OH 4-CH₂CH=CH₂ | H | orange powdered (chloroform) | 205.0–207.0 |
| 60 | 2-CH₂CH=CH₂ 3-OH 4-CH₂CH=CH₂ | H | yellow powdered (ethyl acetate-n-hexane) | 184.0–185.0 |
| 61 | 1-CH₂CH=CH₂ 4-OH | H | yellow powdered (chloroform-n-hexane) | 213.0–216.0 |
| 62 | 3-CH₂CH=CH₂ 4-OH | H | orange powdered (chloroform-n-hexane) | 173.0–174.0 |
| 63 | 1-SCH₃ 4-OH | H | orange powdered (chloroform-methanol) | 262.0–265.0 |
| 64 | 1-SCH₃ 3-CH₂CH=CH₂ 4-OH | H | yellow powdered (chloroform-n-hexane) | 196.0–198.0 |
| 65 | H | 5-CH₃ 7-Br 8-OH | reddish orange oily | — |
| 66 | H | 5-CH₃ 8-OCH₃ | yellow needle-like crystals (ethanol) | 121.0–123.0 |
| 67 | H | 5-CH₃ 8-OCH₂CH=CH—CH₃ | yellow prism-like crystals (ethanol) | 99.0–101.0 |
| 68 | H | 5-CH₃ 7-CH(CH₃)—CH=CH₂ 8-OH | yellow powdered (n-hexane-ethanol) | 76.0–78.0 |
| 69 | H | 5-CH₃ 8-OH | yellow needle-like crystals (ethanol) | 124.0–125.0 |
| 70 | 1-OCH₂CH=CH₂ | H | yellow oily | — |
| 71 | 3-OCH₂CH=CH₂ | H | yellow needle-like crystals (ethanol) | 81.0–83.0 |
| 72 | 4-OCH₂CH=CH₂ | H | yellow needle-like crystals (ethanol) | 112.0–114.0 |
| 73 | 2-OCH₂CH=CH₂ | H | yellow plate crystals (ethanol) | 79.0–81.0 |
| 74 | 2-OCH₃ | 5-OCH₃ | orange needle-like crystals (n-hexane) | 131.0–133.0 |
| 75 | H | 5-CH₃ 8-OCH₂CH=CH₂ | orange oily |  |
| 76 | 2-OCH₂CH=CH₂ 3-CH₂CH=CH₂ | 5-OCH₂CH=CH₂ 6-CH₂CH=CH₂ | red oily |  |
| 77 | 1-OCH₂CH=CH₂ | 7-OCH₂CH=CH₂ | yellow needle-like crystals (ethanol) | 79.0–80.0 |
| 78 | 1-OCH₃ | 7-OCH₃ | yellow powdered (ethanol) | 124.0–126.0 |
| 79 | 2-OCH₂CH=CH₂ 3-OCH₂CH=CH₂ | H | yellow needle-like crystals (ethanol) | 112.0–113.0 |
| 80 | 2-OCH₃ 3-OCH₃ | H | yellow scaly crystals (ethanol) | 162.0–164.0 |
| 81 | 2-OH | 5-OCH₃ | red powdered (chloroform-diethyl ether) | 210.0–212.0 |
| 82 | 1-OCH₃ | H | yellow prism-like crystals (n-hexane-ethyl acetate) | 144.0–145.0 |
| 83 | 3-OCH₃ | H | yellow needle-like crystals (n-hexane-ethyl acetate) | 99.0–100.0 |
| 84 | 1-SCH₃ 4-OCH₃ | H | orange powdered (n-hexane-ethyl acetate) | 180.0–183.0 |
| 85 | 2-OCH₃ | 7-OCH₃ | red needle-like crystals (ethanol) | 123.0–124.0 |
| 86 | 2-OH | 7-OCH₃ | violet powdered (chloroform) | 188.0–192.0 |
| 87 | 2-OCH₃ | 6-OCH₃ | yellow needle-like crystals (ethanol) | 126.0–128.0 |

TABLE 4-continued

| Example | (R¹)ₚ | (R²)_q | Shape of crystals (Solvent for recrystallization) | Melting point (° C.) |
|---|---|---|---|---|
| 88 | 2-OCH₂CH=CH₂ | 5-OCH₂CH=CH₂ | orange needle-like crystals (ethanol) | 75.0–76.0 |
| 89 | 2-OH | 7-Br | reddish orange oily | — |
| 90 | 2-OCH₂CH=CH₂ | 7-Br | yellow powdered (ethanol) | 123.0–124.0 |
| 91 | 2-OH 3-CH₂CH=CH₂ | 7-Br | red powdered | — |
| 92 | 1-CH₂CH=CH₂ 2-OCH₂CH=CH₂ | 7-Br | yellow powdered (ethyl acetate-n-hexane) | 83.0–84.0 |
| 93 | 2-OCH₂CH=CH₂ | 6-OCH₂CH=CH₂ | yellow needle-like crystals (ethanol) | 79.0–80.0 |
| 94 | 2-OCH₂CH=CH₂ | 7-OCH₂CH=CH₂ | orange needle-like crystals (ethanol) | 89.0–90.0 |
| 95 | 1-SCH₃ 4-OCH₂CH=CH₂ | H | yellow powdered (n-hexane-ethyl acetate) | 126.0–127.0 |
| 96 | 2-OCH₃ | H | yellow needle-like crystals (ethyl acetate-n-hexane) | 75.0–76.0 |
| 97 | H | 5-CH₃ 7-CH₃ 8-OCH₃ | reddish orange oily | — |
| 98 | 2-OCH₂CH=CH₂ 3-CH₂CH=CH₂ | 6-CH₂CH=CH₂ 7-OCH₂CH=CH₂ | orange needle-like crystals (ethyl acetate-n-hexane) | 103.0–105.0 |
| 99 | 2-OCH₃ 3-OCH₃ | 6-OCH₃ 7-OCH₃ | orange needle-like crystals (ethyl acetate-n-hexane) | 194.0–195.0 |
| 100 | 2-OCH₃ 3-OCH₃ | 5-OCH₃ | orange needle-like crystals (chloroform-n-hexane) | 184.0–186.0 |
| 101 | 2-OCH₃ 3-OCH₃ | 7-OCH₃ | orange needle-like crystals (chloroform-n-hexane) | 164.0–165.0 |
| 102 | 2-OCH₂CH=CH₂ 3-OCH₂CH=CH₂ | 5-OCH₂CH=CH₂ | orange needle-like crystals (n-hexane) | 77.0–79.0 |
| 103 | 2-OCH₂CH=CH₂ 3-OCH₂CH=CH₂ | 6-OCH₂CH=CH₂ 7-OCH₂CH=CH₂ | orange needle-like crystals (chloroform-n-hexane) | 99.0–100.0 |
| 104 | 2-OCH₂CH=CH₂ 3-OCH₂CH=CH₂ | 7-OCH₂CH=CH₂ | orange powdered (chloroform-n-hexane) | 116.0–117.0* |
| 105 | 2-OH | 5-OCH₃ | red powdered (chloroform-diethyl ether) | 210.0–212.0 |
| 106 | 1-CH₂CH—CH₂ (epoxide) 2-OC(=O)CH₃ | 6-CH₂CH—CH₂ (epoxide) 7-OC(=O)CH₃ | yellow needle-like crystals (dichloromethane-n-hexane) | 170.0–172.0 |
| 107 | 2-OC(=O)CH₃ 3-CH₂CH=CH₂ | 5-OC(=O)CH₃ 6-CH₂CH=CH₂ | yellow needle-like crystals (dichloromethane-n-hexane) | 155.0–156.0 |
| 108 | 2-OC(=O)CH₃ 3-CH₂CH=CH | 5-OC(=O)CH₃ 8-CH₂CH=CH₂ | yellow needle-like crystals (ethyl acetate-n-hexane) | 137.0–138.0 |

*When repeating recrystallization, 116.5–117.0° C.

COMPOUND OF EXAMPLE 65

¹H-NMR (CDCl₃, δ ppm); 2.44 (3H, s), 7.35 (1H, s), 7.43–7.70 (4H, m), 9.00 (1H, s).

COMPOUND OF EXAMPLE 70

¹H-NMR (CDCl₃, δ ppm); 4.73–4.83 (2H, m), 5.31–5.36 (1H, m), 5.51–5.59 (1H, m), 7.29 (1H, ddd, J=1.5 Hz, J=7 Hz, J=7 Hz), 7.37–7.51 (3H, m), 7.64 (1H, d, J=7.5 Hz).

COMPOUND OF EXAMPLE 75

$^1$H-NMR (CDCl$_3$, δ ppm); 2.53 (3H, s), 4.72 (2H, dd, J=1.5 Hz, J=3 Hz), 4.70–4.77 (2H, m), 5.28–5.37 (1H, m), 5.50–5.60 (1H, m), 6.01–6.18 (1H, m), 6.73 (1H, d, J=8.5 Hz), 7.18 (1H, d, J=8.5 Hz), 7.30 (1H, d, J=7.5 Hz), 7.46 (1H, dd, J=7.5 Hz, J=7.5 Hz), 7.62 (1H, d, J=7.5 Hz), 7.66 (1H, dd, J=7.5 Hz, J=7.5 Hz).

COMPOUND OF EXAMPLE 76

$^1$H-NMR (CDCl$_3$, δ ppm); 3.45 (2H, d, J=6.5 Hz), 3.93 (2H, d, J=6.5 Hz), 4.90–5.50 (8H, m), 5.87–6.23 (4H, m), 6.92 (1H, s), 7.07–7.17 (1H, m), 7.33–7.40 (1H, m), 7.55 (1H, s).

COMPOUND OF EXAMPLE 89

$^1$H-NMR (CDCl$_3$, δ ppm); 6.95 (1H, dd, J=2.5 Hz, J=8 Hz), 7.11 (1H, d, J=2.5 Hz), 7.28 (1H, d, J=8 Hz), 7.35 (1H, d, J=8 Hz), 7.55 (1H, dd, J=2 Hz, J=8 Hz), 7.70 (1H, d, J=2 Hz), 8.23 (1H, s).

COMPOUND OF EXAMPLE 91

$^1$H-NMR (CDCl$_3$, δ ppm); 3.44 (2H, d, J=6.5 Hz), 5.15–5.23 (2H, m), 5.92–6.07 (1H, m), 7.09–7.30 (4H, m), 7.52 (1H, dd, J=2 Hz, J=8 Hz), 7.65 (1H, d, J=2 Hz).

COMPOUND OF EXAMPLE 97

$^1$H-NMR (CDCl$_3$, δ ppm); 2.25 (3H, s), 2.30 (3H, s), 3.92 (3H, s), 7.15 (1H, s), 7.41–7.68 (4H, m).

By using a suitable starting material, the following compounds were obtained according to the same manner as that described in Example 1.

TABLE 5

| Example | (R$^1$)$_p$ | (R$^2$)$_q$ | Shape of crystals (Solvent for recrystalization) | Melting point (° C.) |
|---|---|---|---|---|
| 109 | 1-(CH$_2$)$_2$CH$_3$<br>2-OH<br>3-(CH$_2$)$_2$CH$_3$ | H | red needle-like crystals (ethanol-water) | 157–158 |
| 110 | 1-(CH$_2$)$_2$CH$_3$<br>2-OH | 5-OH<br>6-(CH$_2$)$_2$CH$_3$ | red powdered (ethanol-water) | 158–160 |
| 111 | 1-CH$_2$CH=CH$_2$<br>2-OCOCH$_3$<br>3-OCOCH$_3$<br>4-CH$_2$CH=CH$_2$ | H | yellow needle-like crystals (ethyl acetate) | 167–168 |
| 112 | 1-CH$_3$<br>2-OH<br>3-CH$_3$ | 5-OH | red needle-like crystals (ethanol-water) | 247–249 |
| 113 | 2-OH<br>3-Br | 5-OH<br>8-Br | red powdered (ethanol-water) | more than 300 |
| 114 | 1-CH(CH$_3$)$_2$<br>2-OH<br>3-CH(CH$_3$)$_2$ | 5-OH | red needle-like crystals (ethyl acetate-n-hexane) | 211–213 |
| 115 | 1-CH$_3$<br>2-OH<br>3-CH$_3$ | 5-OH<br>6-CH$_2$N(CH$_3$)$_2$ | red needle-like crystals (toluene) | 190–191 |
| 116 | 1-CH$_3$<br>2-OH<br>3-CH$_3$ | 5-OH<br>6-CH$_2$N(CH$_3$)$_2$<br>8-CH$_2$N(CH$_3$)$_2$ | orange needle-like crystals (toluene-n-hexane) | 181–182 |
| 117 | 1-CH(CH$_3$)$_2$<br>2-OH<br>3-CH(CH$_3$)$_2$ | 5-OH<br>6-CH$_2$N(CH$_3$)$_2$ | red needle-like crystals (toluene-n-hexane) | 198–200 |
| 118 | 1-CH$_3$<br>2-OH<br>3-CH$_3$ | 5-OH<br>6-CH$_3$ | orange needle-like crystals (acetonitrile) | 254–256 |
| 119 | 1-CH$_3$ | 5-OH | orange needle-like crystals | more than 300 |

TABLE 5-continued

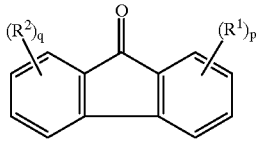

| Example | (R¹)ₚ | (R²)q | Shape of crystals (Solvent for recrystalization) | Melting point (° C.) |
|---|---|---|---|---|
|  | 2-OH<br>3-CH₃ | 6-CH₃<br>8-CH₃ | (acetonitrile) |  |
| 120 | 1-CH₃<br>2-OH<br>3-CH₃ | 5-OH<br>6-CH₂—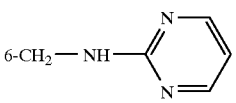 | brown needle-like crystals (dichloromethane-methanol) | 285–287 |
| 121 | 1-CH₃<br>2-OH<br>3-CH₃ | 5-OH<br>6-CH₂NHCH₂CO₂C₂H₅ | red powdered (toluene-n-hexane) | 138–139 |
| 122 | 1-(CH)₂CH₃<br>2-OH<br>3-CH₂N(CH₃)₂ | 5-OH<br>6-(CH)₂CH₃ | red needle-like crystals (toluene) | 208–213 |
| 123 | 1-CH₃<br>2-OH<br>3-CH₃ | 5-OH<br>6-CH₂—NH—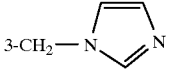 | orange powdered (ethyl acetate) | 278–280 |
| 124 | 1-(CH₂)₂CH₃<br>2-OH<br>3-CH₂NHCH₂CO₂C₂H₅ | 5-OH<br>6-(CH₂)₂CH₃ | red needle crystals (toluene-n-hexane) | 129–130 |
| 125 | 1-CH₃<br>2-OH<br>3-CH₃ | 5-OH<br>6-CH₂OCH₃ | red needle-like crystals (toluene-n-hexane) | 178–179 |
| 126 | 1-(CH₂)₂CH₃<br>2-OH<br>3-CH₂—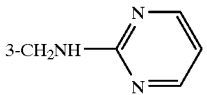 | 5-OH<br>6-(CH₂)₂CH₃ | red needle crystals (ethanol-water) | 250–252 |
| 127 | 1-(CH₂)₂CH₃<br>2-OH<br>3-CH₂NH—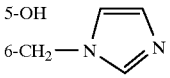 | 5-OH<br>6-(CH₂)₂CH₃ | orange powdered (acetonitrile) | 239–241 |
| 128 | 1-CH—CH₃<br>　　　＼<br>　　　　CH₃<br>2-OH<br>3-CH—CH₃<br>　　　＼<br>　　　　CH₃ | 5-OH<br>6-CH₂—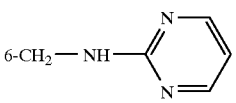 | red powdered (toluene) | 236–237 |
| 129 | 1-(CH₂)₂CH₃<br>2-OH<br>3-CH₂OCH₃ | 5-OH<br>6-(CH₂)₂CH₃ | orange needle-like crystals (toluene-n-hexane) | 194–195 |
| 130 | 1-(CH₂)₂CH₃<br>2-OH<br>3-CH₂NH—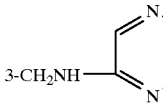 | 5-OH<br>6-(CH₂)₂CH₃ | red needle-like crystals (acetonitrile) | 204–205 |
| 131 | 1-(CH₂)₂CH₃<br>2-OH | 5-OH<br>6-(CH₂)₂CH₃ | red sacley crystals (isopropyl ether) | 145–146 |

TABLE 5-continued

[Fluorenone structure with (R²)q and (R¹)p substituents]

| Example | (R¹)p | (R²)q | Shape of crystals (Solvent for recrystalization) | Melting point (° C.) |
|---|---|---|---|---|
| 132 | 3-CH₂NH—CH(CO₂CH₃)—CH₂CH(CH₃)—CH₃<br>1-(CH₂)₂CH₃<br>2-OH<br>3-CH₂—[pyrrolidine-N, 2-CO₂CH₃] | 5-OH<br>6-(CH₂)₂CH₃ | red needle crystals<br>(toluene-n-hexane) | 123–124 |
| 133 | 1-CH₃<br>2-OH<br>3-CH₃ | 5-OH<br>6-CH₂N[piperazine]N—CH₃ | orange powdered<br>(dimethylformamide-water) | 262–264 |
| 134 | 1-(CH₂)₂CH₃<br>2-OCOCH₃<br>3-(CH₂)₂CH₃ | 5-OCOCH₃<br>6-(CH₂)₂CH₃<br>8-(CH₂)₂CH₃ | yellow needle crystals<br>(acetonitrile) | 142–143 |
| 135 | 1-CH₃<br>2-OH<br>3-CH₃ | 5-OH<br>6-CH₂S—[2-pyridyl] | orange powdered<br>(toluene) | 219.5–221.0 |
| 136 | 1-CH₃<br>2-OH<br>3-CH₃ | 5-OH<br>6-CH₂S—[phenyl] | orange needle-like crystals<br>(toluene) | 205–206.5 |
| 137 | 1-CH₃<br>2-OH<br>3-CH₃ | 5-OH<br>6-CH₂S—[benzimidazol-2-yl] | red powdered<br>(dichloromethane-n-hexane) | 252.5–255.5 |
| 138 | 1-CH₃<br>2-OH<br>3-CH₃ | 5-OH<br>6-CH₂S—[imidazol-2-yl] | brown powdered<br>(toluene-n-hexane) | 278–279.5 |
| 139 | 1-CH(CH₃)CH₃<br>2-OH<br>3-CH(CH₃)CH₃ | 5-OH<br>6-CH₂N(CH₃)₂<br>8-CH₂N(CH₃)₂ | orange powdered<br>(toluene-n-hexane) | 157.8–159 |
| 140 | 1-CH₃<br>2-OH<br>3-CH₃ | 5-OH<br>6-CHO | brown needle-like crystals<br>(dichloromethane-acetone) | 288.5–290.5 |

TABLE 5-continued

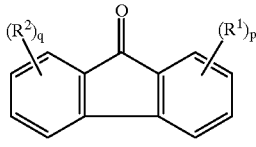

| Example | (R¹)ₚ | (R²)_q | Shape of crystals (Solvent for recrystalization) | Melting point (° C.) |
|---|---|---|---|---|
| 141 | 1-CH₃<br>2-OH<br>3-CH₃ | 5-OH<br>6-CH₂S—⌬—OCH3 | orange needle-like crystals (acetonitrile) | 200–201 |
| 142 | 1-CH₃<br>2-OH<br>3-CH₃ | 5-OH<br>6-CH₂S—⌬ | orange powdered (toluene-n-hexane) | 165.5–167 |
| 143 | 1-CH₂CH—CH₃<br>　　　＼<br>　　　O(CH₂)₂O(CH₂)₂OH<br>2-OH<br>3-(CH₂)₂CH₃ | 5-OH<br>6-(CH₂)₂CH₃<br>8-(CH₂)₂CH₃ | yellow needle-like crystals<br>(toluene-n-hexane) | 136.5–137 |
| 144 | 1-CH₃<br>2-OH<br>3-CH₃ | 5-OH<br>6-CH₂CN | orange needle crystals (acetonitrile) | 254.5–255.5 |
| 145 | 2-OH<br>3-(CH₂)₂CH₃ | 5-OH<br>6-(CH₂)₂CH₃<br>8-(CH₂)₂CH₃ | Brown needle-like crystals (toluene) | 194.6–195.8 |
| 146 | 1-(CH₂)₂CH₃<br>2-OH<br>3-(CH₂)₂CH₃ | 5-OH<br>6-(CH₂)₂CH₃ | Orange needle-like crystals (toluene-n-hexane) | 203.4–204.8 |
| 148 | 1-Cl<br>2-OCH₂CH₂=CH₂<br>3-Cl | 5-OCH₂CH₂=CH₂<br>8-Cl | yellow needle-like crystals (dichloromethane-n-hexane) | 132–134 |
| 149 | 2-OCH₂CH₂=CH₂<br>3-Cl | 5-OCH₂CH₂=CH₂<br>6-Cl | yellow needle-like crystals (dichloromethane-n-hexane) | 117–118 |
| 150 | 2-OCH₂CH₂=CH₂<br>3-Cl | 5-OCH₂CH=CH₂<br>8-Cl | yellow needle-like crystals (dichloromethanbe-n-hexane) | 158–160 |
| 151 | 1-CH₃<br>2-OCH₃<br>3-CH₃ | 5-OCH₃ | orange partciculate crystals (n-hexane) | 100–102 |
| 152 | 1-CH₃<br>2-OH<br>3-CH₃ | 5-OH<br>6-CH₂N⁺(CH₃)₃ | orange powdered (nitromethane-diethyl ether) | 228.5–229.5 (I⁻) |
| 153 | 1-CH—CH₃<br>　　＼<br>　　CH₃<br>2-OCH₃<br>3-CH—CH₃<br>　　＼<br>　　CH₃ | 5-OCH₃ | yellow powdered<br><br>(ethyl acetate-n-hexane) | 122.5–124 |

EXAMPLE 154

To ethanol (90 ml), a 50% dimethylamine solution (4.5 g) and paraformaldehyde (1.5 g) were added and the mixture was stirred at 100° C. for 20 minutes. To this was added 1,3-dimethyl-2,5-dihydroxyfluorenone (3.0 g), followed by stirring at 100° C. for 24 minutes. After the solvent was distilled off, the residue was purified by silica gel column chromatography (eluent: n-hexane/ethyl acetate (4:1)) and recrystallized from toluene to give 2.1 g of 1,3-dimethyl-6-dimethylaminomethyl-2,5-dihydroxyfluorenone as a red needle-like crystal.

Melting point: 190.0–191.0° C.

EXAMPLE 155

To acetic acid (30 ml), a 50% dimethylamine solution (1.5 g) and paraformaldehyde (0.5 g) were added and the mixture was stirred at 120° C. for 20 minutes. To this was added 1,3-dimethyl-2, 5-dihydroxyfluorenone (1.0 g), followed by stirring at 120° C. for 8 hours. The reaction solution was neutralized with an aqueous 20% sodium hydroxide solution and extracted with dichloromethane, then the extract was dried over magnesium sulfate. The solvent was distilled off and the residue was recrystallized from toluene-n-hexane to give 750 mg of 1,3-dimethyl-6,8-bisdimethylaminomethyl-2,5-dihydroxyfluorenone as an orange needle-like crystal.

Melting point: 181.0–182.0° C.

By using a suitable starting material, compounds of the above Examples 117, 122 and 139 were obtained according to the same manner as that described in Examples 155 and 156.

EXAMPLE 156

To ethanol (20 ml), 6-dimethylaminomethyl-2,5-dihydroxyfluorenone (200 mg), 10% palladium-carbon (10 mg) and ammonium formate (212 mg) were added and the mixture was stirred at 90° C. for 10 minutes. After the catalyst was removed, the reaction solution was concentrated and recrystallized from acetonitrile to give 156 mg of 1,3,6-trimethyl-2,5-dihydroxyfluorenone as an orange needle-like crystal.

Melting point: 254.0–256.0° C.

By using a suitable starting material, compounds of the above Examples 11, 12, 65 to 69, 75, 97, 112, 115, 116, 119 to 121, 123, 125, 133, 135 to 138, 140 to 142, 144, 151 and 152 were obtained according to the same manner as that described in Examples 156.

EXAMPLE 157

To a mixed liquid of acetonitrile (100 ml) and dimethylformamide (20 ml), 3-dimethyl-6-trimethylammoniummethyl-2,5-dihydroxyfluorenone iodide (550 mg) and imidazole (427 mg) were added and the mixture was stirred at 90° C. for 30 minutes. After the solvent was distilled off, the residue was purified by silica gel column chromatography (eluent: dichloromethane/methanol (20:1)) and recrystallized from dichloromethane-methanol to give 217 mg of 1,3-dimethyl-6-(1-imidazolylmethyl-2, 5-dihydroxyfluorenone as a brown powder.

Melting point: 285.0–287.0° C.

EXAMPLE 158

1,3-Dimethyl-6-trimethylammoniummethyl-2,5-dihydroxyfluorenone iodide (420 mg) was added to methanol (42 ml) and the mixture was stirred at 90° C. for 24 hours. After the solvent was distilled off, the residue was purified by silica gel column chromatography (eluent: n-hexane/ethyl acetate (4:1)) and recrystallized from toluene-n-hexane to give 100 mg of 1,3-dimethyl-6-methoxymethyl-2,5-dihydroxyfluorenone as a red needle-like crystal.

Melting point: 178.0–179.0° C.

EXAMPLE 159

To a mixed liquid of acetonitrile (60 ml) and dimethylformamide (9 ml), hydrochloric acid glycine ethyl ester (477 mg) and potassium carbonate (472 mg) were added and the mixture was stirred at 90° C. for one hour. To this was added 1,3-dimethyl-6-trimethylammoniummethyl-2,5-dihydroxyfluorenone iodide (300 mg), followed by stirring at 90° C. for one hour. After the solvent was distilled off, ethyl acetate was added to the residue and potassium carbonate was filtered. After the solvent was distilled off, the residue was purified by silica gel column chromatography (eluent: n-hexane/ethyl acetate (3:1)) and recrystallized from toluene-n-hexane to give 150 mg of 1,3-dimethyl-6-ethoxycarboxylmethylaminomethyl-2,5-dihydroxyfluorenone as a red powder.

Melting point: 138.0–139.0° C.

By using a suitable starting material, compounds of the above Examples 115 to 117, 122, 123, 124, 126 to 133 and 139 were obtained according to the same manner as that described in Examples 157 to 159.

EXAMPLE 160

To dimethylformamide (2 ml), 1,3-dimethyl-6-dimethylaminomethyl-2,5-dihydroxyfluorenone (150 mg) and 2-mercaptopyridine (168 mg) were added and the mixture was stirred at 150° C. for 3.5 hours. After the solvent was distilled off, the residue was purified by silica gel column chromatography (eluent: n-hexane/ethyl acetate (5:1)) and recrystallized from toluene to give 90 mg of 1,3-dimethyl-6-(2-pyridylthio)methyl-2,5-dihydroxyfluorenone as an orange powder.

Melting point: 219.6–221° C.

By using a suitable starting material, compounds of the above Examples 136 to 138, 141 and 142 were obtained according to the same manner as that described in Example 160.

Pharmacological test 1

Nerve cells of the cerebral cortex were removed aseptically from a fetal rat (17 days-old) and cultured according to a Asou's method [Asou, H. Brain Res., 332; pages 355–357 (1985)]. After the meninx, blood vessel, etc. were removed from the cerebral hemisphere, they were put through a stainless steel mesh (pore size: 140μm). Then, the isolated cells were floated on a culture medium (Eagle's basal medium containing 10% fetal bovine serum and glucose of 1 g/l) and $1.5 \times 10^6$ cells were respectively seeded on a dish (diameter: 35 mm) coated with poly-L-lysine to initiate the culture (37° C., 3% $CO_2$). After 24 hours, the culture medium was replaced by a culture medium containing a test compound and cultured for additional 9 days.

10 Days after initiation of the culture, neurite sprouting (NS) was evaluated under phase contrast microscopy by comparing with the control group. The results are shown in Table 6 below.

(++): extremely strong in comparison with the control
(+): strong in comparison with the control
(±): same as the control
(−): inferior to the control

TABLE 6

| Test Compound | Dose (mole) | Culture |
|---|---|---|
| Compound of Example 11 | $10^{-5}$ | NS (+) |
| Compound of Example 14 | $10^{-7}$ | NS (++) |
| Compound of Example 16 | $10^{-7}$ | NS (+) |
| Compound of Example 17 | $10^{-5}$ | NS (++) |
| Compound of Example 18 | $10^{-5}$ | NS (++) |
| Compound of Example 19 | $10^{-5}$ | NS (++) |
| Compound of Example 21 | $10^{-7}$ | NS (++) |
| Compound of Example 26 | $10^{-7}$ | NS (+) |
| Compound of Example 27 | $10^{-5}$ | NS (+) |
| Compound of Example 28 | $10^{-5}$ | NS (++) |
| Compound of Example 31 | $10^{-7}$ | NS (+) |
| Compound of Example 35 | $10^{-7}$ | NS (+) |
| Compound of Example 40 | $10^{-5}$ | NS (++) |
| Compound of Example 45 | $10^{-7}$ | NS (+) |
| Compound of Example 47 | $10^{-6}$ | NS (+) |
| Compound of Example 48 | $10^{-6}$ | NS (+) |
| Compound of Example 49 | $10^{-6}$ | NS (+) |
| Compound of Example 60 | $10^{-7}$ | NS (+) |
| Compound of Example 61 | $10^{-5}$ | NS (++) |
| Compound of Example 62 | $10^{-6}$ | NS (++) |
| 0.5% Ethanol | — | NS (±) |

Pharmacological Test 2

(The measurement of neurite outgrowth in primary culture of mouse dorsal root ganglion cells)

Preparation of cells was conducted according to a method of Horie et al. [H. Horie., FEBS, 296, 23 (1990)]. That is, C57BL/6 male mice aged 10 to 15 weeks were used. They were bleeded to death under ether anesthetization and the backbone from cervical vertebra to sacral vertebra was removed. The capsule of dorsal root ganglion of which ventral root and dorsal root had been cut was stripped in a Ham F12 medium (Flow laboratories) and then ganglia were treated with 0.25% collagenase (Worthington Biochemical Corporation) at 37° C. for 90 minutes. The medium was replaced by a Hank's physiological buffer solution containing no calcium and magnesium and cells were treated with 0.25% trypsin (Flow Laboratories) at room temperature for 20 minutes. A trypsin inhibitor (Sigma, 100 μg/ml) was added to terminate the enzyme reaction and trituration was conducted 20 times using a tapered Pasteur pipette. The medium was replaced again by the Ham F12 medium and cells were put through a nylon mesh (150 μm) to remove a cell mass which had not been separated. Cells were suspended in the Ham F12 medium containing a N1 additive [Bottenstein, J. E., Exp. Cell. Res., 125, 183 (1980)] (kanamycin of 60 μg/ml added).

A poly-1-lysine-coating cell disc as a culture medium which had been subjected to 10 μg/ml laminin (Koken Cell Gen) coating treatment at 37° C. for 3 hours was placed on a 24 well dish and nerve cells (5000 to 10000 cells/dish) were seeded. The test compound (concentration: 0.01 mol/l) was dissolved in dimethyl sulfoxide and diluted with a phosphate buffer solution to adjust to a final concentration, and then added to a culture solution. Cells were cultured in 5% $CO_2$-95% air phase at 37° C. for 7 days.

For the measurement of neurite outgrowth, the cell disc was washed with a phosphate buffer solution 7 days after initiation of the culture and immobilized with 4% paraformaldehyde at 4° C. for 24 hours, and then immune staining was conducted with Vecstatin ABC kit (Vector) using a neurofilament antibody (200 kD, manufactured by Boehringer Mannheim GmbH). The periphery of the cell disc was restrictively observed under microscopy, and the amount of neurofilament (whole length per well) was evaluated by comparing with the control well according to the following criteria: positive (+), false positive (±) and negative (−). The results are shown in Table 7 below.

TABLE 7

| Test Compound | Dose (mole) | Neurite outgrowth action |
|---|---|---|
| Compound of Example 17 | $10^{-6}$ | + |
| Compound of Example 18 | $10^{-6}$ | + |
| Compound of Example 19 | $10^{-7}$ | + |
| Compound of Example 20 | $10^{-6}$ | + |
| Compound of Example 21 | $10^{-7}$ | + |
| Compound of Example 22 | $10^{-7}$ | + |
| Compound of Example 26 | $10^{-7}$ | + |
| Compound of Example 27 | $10^{-7}$ | + |
| Compound of Example 29 | $10^{-7}$ | + |
| Compound of Example 30 | $10^{-7}$ | + |
| Compound of Example 31 | $10^{-7}$ | + |
| Compound of Example 32 | $3 \times 10^{-8}$ | + |
| Compound of Example 33 | $10^{-7}$ | + |
| Compound of Example 34 | $10^{-7}$ | + |
| Compound of Example 36 | $10^{-6}$ | + |
| Compound of Example 38 | $10^{-7}$ | + |
| Compound of Example 39 | $10^{-7}$ | + |
| Compound of Example 40 | $10^{-6}$ | + |
| Compound of Example 41 | $10^{-7}$ | + |
| Compound of Example 44 | $10^{-7}$ | + |
| Compound of Example 45 | $10^{-7}$ | + |
| Compaund of Example 47 | $10^{-7}$ | + |
| Compound of Example 48 | $10^{-7}$ | + |
| Compound of Example 49 | $10^{-7}$ | + |

TABLE 7-continued

| Test Compound | Dose (mole) | Neurite outgrowth action |
|---|---|---|
| Compound of Example 50 | $10^{-7}$ | + |
| Compound of Example 53 | $10^{-7}$ | + |
| Compound of Example 54 | $10^{-7}$ | + |
| Compound of Example 60 | $10^{-6}$ | + |
| Compound of Example 62 | $10^{-6}$ | + |
| Compound of Example 63 | $10^{-6}$ | + |
| Compound of Example 64 | $10^{-6}$ | + |
| Compound of Example 106 | $10^{-7}$ | + |
| Compound of Example 108 | $10^{-7}$ | + |
| Compound of Example 118 | $3 \times 10^{-7}$ | + |
| Compound of Example 123 | $10^{-7}$ | + |
| Compound of Example 127 | $10^{-7}$ | + |
| Compound of Example 131 | $10^{-7}$ | + |
| Compound of Example 132 | $10^{-7}$ | + |
| Compound of Example 134 | $3 \times 10^{-8}$ | + |
| Compound of Example 136 | $3 \times 10^{-7}$ | + |
| Compound of Example 141 | $3 \times 10^{-8}$ | + |
| Compound of Example 142 | $3 \times 10^{-8}$ | + |
| Compound of Example 143 | $10^{-7}$ | + |
| Compound of Example 144 | $10^{-7}$ | + |

Pharmacological test 3

(The measurement of antioxidation action)

The antioxidation action was measured using the hyperoxidation reaction of lipid due to ascorbic acid induction [Shimada, O. and Yasuda, H. BBA489, 163–172 (1977)].

Microsome fraction was obtained from a lever of Wister rat by a Kato's method [J. Biochem., 59, 574 (1966)]. This fraction was added to a 60 mM potassium phosphate buffer solution (containing 45 mM potassium chloride, 200 μM ascorbic acid and 20 μM ferrous sulfate) in an amount of 1 mg/ml and the test compound (0.1% dimethyl sulfoxide) was added, and the mixture was incubated at 37° C. for 15 minutes. The same amount of 10% trichloroacetic acid was added and the resultant was centrifuged. A portion of the supernatant was collected and the amount of malondialdehyde due to thiobarbituric acid (TBA value) was measured [Klaassen, C. D. and Plaa, G. L. Biochem. Pharmacol., 18: 2019 (1969)]. The inhibition ratio was calculated by the following formula:

Inhibition ratio={1-(TBA value of specimen)/(TBA value of control)}×100, and 50% inhibition concentration ($IC_{50}$) is shown in Table 8.

TABLE 8

| Test compound | $IC_{50}$ (μM) |
|---|---|
| Compound of Example 21 | 0.1 |
| Compound of Example 27 | 1.6 |
| Compound of Example 31 | 0.2 |
| Compound of Example 47 | 0.2 |
| Compound of Example 49 | 2.1 |

Pharmacological test 4

(C-GMP-PDE (type V) inhibition action)

The separation and purification of PDE from a human blood platelet was conducted according to a method of Hidaka et al. [Hidaka, H. and Asano, I., Biochem. Biophys. Acta 429, 485–497 (1976)]. That is, a blood platelet derived from a healthy adult was washed with water, floated with a Tris buffer solution and centrifuged. Then, the supernatant thereof was applied to DEAE-cellulose and separated into three fractions, FI, FII and FIII due to concentration gradient of sodium acetate. By using FI having high affinity to C-GMP, the inhibition action of the test compound was examined. The influence of the drug on PDE was represented by the inhibition ratio to PDE activity in the absence of the drug. The results are shown in Table 9.

TABLE 9

| Test compound | IC$_{50}$ ($\mu$M) |
| --- | --- |
| Compound of Example 21 | 14.7 |
| Compound of Example 27 | 8.7 |
| Compound of Example 31 | 0.4 |
| Compound of Example 47 | 3.4 |
| Compound of Example 49 | 2.2 |

We claim:
1. A fluorenone derivative represented by the formula:

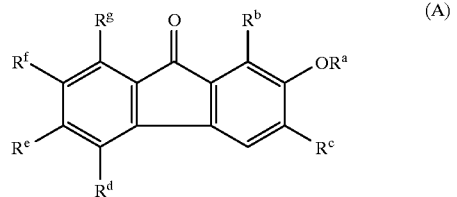

wherein $R^a$ is a lower alkenyl group or an acetyl group;
$R^b$ and $R^c$ are the same or different and are a hydrogen atom, a lower alkenyl group, a lower alkyl group, a halogen atom, a lower alkoxy group, a lower alkylthio group, a lower alkenyloxy group, a group of the formula:

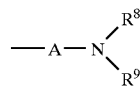

(wherein $R^8$ and $R^9$ are the same or different and indicate a hydrogen atom, a lower alkyl group, a lower alkoxycarbonyl-substituted lower alkyl group, a pyrimidinyl group or pyrazinyl group, and $R^8$ and $R^9$ may bond together with the nitrogen atom to which they are attached to form a 5- or 6-membered saturated heterocycle through a nitrogen or oxygen atom or not, the heterocycle optionally containing a substituent selected from the group consisting of a lower alkyl group and a lower alkoxycarbonyl group; and A is a lower alkylene group), an imidazolyl-substituted lower alkyl group, a lower alkoxy-substituted lower alkyl group, a hydroxyl group-substituted lower alkoxy-lower alkoxy-substituted lower alkyl group or a lower trialkyl-substituted ammonium-substituted lower alkyl group;
$R^d$, $R^e$, $R^f$ and $R^g$ are the same or different and are a hydrogen atom, a lower alkenyl group, a lower alkyl group, a halogen atom, a lower alkoxy group, a lower alkenyloxy group, a group of the formula:

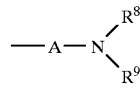

(wherein $R^8$ and $R^9$ are as defined above), an imidazolyl-substituted lower alkyl group, a lower alkoxy-substituted lower alkyl group, a pyridylthio-substituted lower alkyl group, a phenylthio-substituted lower alkyl group optionally containing a lower alkoxy group as a substituent on a phenyl ring, a benzimidazolylthio-substituted lower alkyl group, an imidazolylthio-substituted lower alkyl group, a lower alkanoyl group, a cycloalkylthio-substituted lower alkyl group, a cyano-substituted lower alkyl group or a lower trialkyl-substituted ammonium-substituted lower alkyl group;

(i) $R^c$ and $R^g$ must not be methyl groups when $R^a$, $R^b$, $R^d$, $R^e$ and $R^f$ are hydrogen atoms, (ii) $R^g$ must not be a methyl group when $R^b$, $R^c$, $R^e$ and $R^f$ are hydrogen atoms, and $R^a$ an acetyl group, (iii) $R^b$ must not be an allyl group when $R^c$, $R^d$, $R^e$, $R^f$ and $R^g$ are hydrogen atoms, and $R^a$ is an acetyl group, (iv) $R^a$ must not be an allyl group or an acetyl group when $R^b$, $R^d$, $R^e$, $R^f$ and $R^g$ are hydrogen atoms, (v) any one of $R^d$, $R^e$, $R^f$ and $R^g$ must not be a hydrogen atom when $R^b$ and $R^c$ are hydrogen atoms and any one of $R^d$, $R^e$, $R^f$ and $R^g$ is a lower alkenyl group, or a salt thereof.

2. A fluorenone derivative represented by the formula:

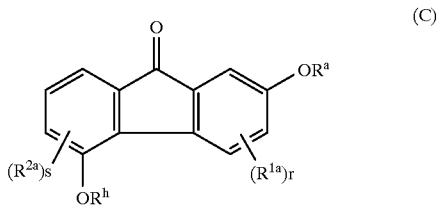

wherein $R^{1a}$ is a hydrogen atom, a lower alkenyl group, a lower alkyl group, a halogen atom, a group of the formula:

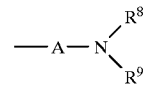

(wherein A, $R^8$ and $R^9$ are as defined in claim 1), an imidazolyl-substituted lower alkyl group, a lower alkoxy-substituted lower alkyl group or a hydroxyl group-substituted lower alkoxy-lower alkoxy-substituted lower alkyl group,
$R^{2a}$ is a lower alkoxy group or lower alkenyloxy group,
$R^a$ and $R^h$ are each a hydrogen atom, a lower alkenyl group or an acetyl group; s is an integer of 1 to 3,
or a salt thereof.

3. A fluorenone derivative represented by the formula:

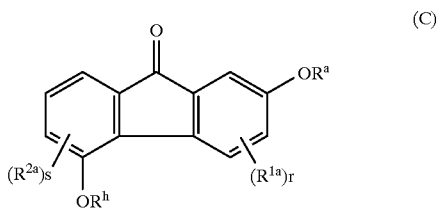

wherein $R^{1a}$ is a lower alkoxy group, a lower alkylthio group, a lower alkanyloxy group or a lower trialkyl-substituted ammonium-substituted lower alkyl group,
$R^{2a}$ is a hydrogen atom, a lower alkoxy, a lower alkenyloxy, a lower alkenyl group, a lower alkyl group, a halogen atom, a group of the formula:

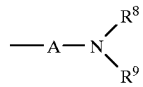

(wherein $R^8$, $R^9$ and A are as defined in claim 1), an imidazolyl-substituted lower alkyl group, a lower alkoxy-substituted lower alkyl group, a pyridylthio-substituted lower alkyl group, a phenylthio-substituted lower alkyl group optionally containing a lower alkoxy group as a substituent on a phenyl ring, benzimidazolylthio-substituted lower alkyl group, an imidazolylthio-substituted lower alkyl group, a lower alkanoyl group, a cycloalkylthio-substituted lower alkyl group, a cyano-substituted lower alkyl group or a lower trialkyl-substituted ammonium-substituted lower alkyl group, $R^a$ and $R^h$ are each a hydrogen atom, a lower alkenyl group or an acetyl group; s is an integer of 1 to 3; provided that,
(1) a 4-position of a fluorenone skeleton must not be substituted with $R^{1a}$ when $R^a$ and $R^h$ are hydrogen atoms or acetyl groups, and $R^{2a}$ are hydrogen atom, r is 1 and $R^{1a}$ is a methoxy group, or a salt thereof.

4. A fluorenone derivative represented by the formula:

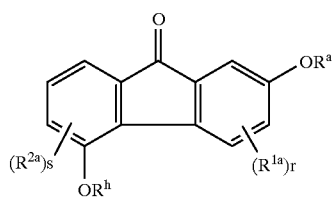

(C)

wherein r and s indicate 1 or 2; 1- and/or 3-positions of a fluorenone skeleton are substituted with $R^{1a}$; 6- and/or 8-positions of the fluorenone skeleton are substituted with $R^{2a}$; when r is 1, $R^{1a}$ has the same meanings as $R^b$ and $R^c$ in claim 1, and when r is 2, one $R^{1a}$ is a hydrogen atom, a lower alkenyl group, a lower alkyl group or a halogen atom and the other $R^{1a}$ is a hydrogen atom, a lower alkyl group, a group of the formula:

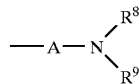

(wherein A, $R^8$ and $R^9$ are as defined in claim 1), a halogen atom, a lower alkenyl group, an imidazolyl-substituted lower alkyl group, a lower alkoxy-substituted lower alkyl group or a hydroxyl group-substituted lower alkoxy-lower alkoxy-substituted lower alkyl group; when s is 1, $R^{2a}$ has the same meanings as $R^d$, $R^e$, $R^f$ and $R^g$ in claim 1, and when s is 2, one $R^{2a}$ is a hydrogen atom, a lower alkyl group, a lower alkenyl group or a group of the formula:

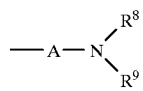

(wherein A, $R^8$ and $R^9$ are as defined in claim 1) and the other $R^{2a}$ is a halogen atom, a group of the formula:

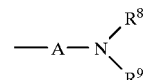

(wherein A, $R^8$ and $R^9$ are as defined in claim 1), a lower alkenyl group, a lower alkyl group, an imidazolyl-substituted lower alkyl group, a lower alkoxy-substituted lower alkyl group, a pyridylthio-substituted lower alkyl group, a phenylthio-substituted alkyl group optionally containing a lower alkoxy group as a substituent on a phenyl ring, benzimidazolylthio-substituted lower alkyl group, an imidazolylthio-substituted lower alkyl group, a lower alkanoyl group, a cycloalkylthio-substituted lower alkyl group, a cyano-substituted lower alkyl group or a lower trialkyl-substituted ammonium-substituted lower alkyl group, $R^a$ and $R^h$ are each a hydrogen atom, a lower alkenyl group or an acetyl group; s is an integer of 1 to 3; provided that,
(1) any one of $R^a$ and $R^h$ is an acetyl group when $R_{1a}$ and $R^{2a}$ are hydrogen atoms, or a salt thereof.

5. The fluorenone derivative according to claim 1, wherein $R^b$ and $R^c$ are a hydrogen atom, a lower alkenyl group or a lower alkyl group, or a salt thereof.

6. The fluorenone derivative according to claim 5, wherein $R^b$ and $R^c$ are a halogen atom, a lower alkoxy group, a lower alkylthio group, a lower alkenyloxy group, a group of the formula:

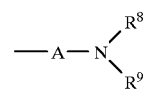

wherein $R^8$ and $R^9$ are the same or different and are a hydrogen atom, a lower alkyl group, a lower alkoxycarbonyl-substituted lower alkyl group, a pyrimidinyl group or pyrazinyl group, and $R^8$ and $R^9$ may bond together with the nitrogen atom to which they are attached to form a 5- or 6-membered saturated heterocycle through a nitrogen or oxygen atom or not, the heterocycle optionally containing a substituent selected from the group consisting of a lower alkyl group and a lower alkoxycarbonyl group; and A is a lower alkylene group, an imidazolyl-substituted lower alkyl group, a lower alkoxy-substituted lower alkyl group, a hydroxyl group-substituted lower alkoxy-lower alkoxy-substituted lower alkyl group or a lower trialkyl-substituted ammonium-substituted lower alkyl group, an imidazolyl-substituted lower alkyl group, a lower alkoxy-substituted lower alkyl group, a hydroxyl group-substituted alkoxy-lower alkoxy-substituted lower alkyl group or a lower trialkyl-substituted ammonium-substituted lower alkyl group, or a salt thereof.

7. The fluorenone derivative according to claim 5, wherein $R^d$, $R^e$, $R^f$ and $R^g$ are a hydrogen atom, a lower alkoxy group, a lower alkyl group, a lower alkenyl group, a lower alkenyloxy group or a halogen atom, or a salt thereof.

8. The fluorenone derivative according to claim 5, wherein $R^d$, $R^e$, $R^f$ and $R^g$ are a group of the formula:

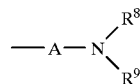

wherein $R^8$ and $R^9$ are the same or different and are a hydrogen atom, a lower alkyl group, a lower alkoxycarbonyl-substituted lower alkyl group, a pyrimidinyl group or pyrazinyl group, and $R^8$ and $R^9$ may bond together with the nitrogen atom to which they are attached to form a 5- or 6-membered saturated heterocycle through a nitrogen or oxygen atom or not, the heterocycle optionally containing a substituent selected from the group consisting of a lower alkyl group and a lower alkoxycarbonyl group; and A is a lower alkylene group, an imidazolyl-substituted lower alkyl group, a lower alkoxy-substituted lower alkyl group, a hydroxyl group-substituted lower alkoxy-lower alkoxy-substituted lower alkyl group or a lower trialkyl-substituted ammonium-substituted lower alkyl group, an imidazolyl-substituted lower alkyl group, a lower alkoxy-substituted lower alkyl group, a pyridylthio-substituted lower alkyl group, a phenylthio-substituted lower alkyl group optionally containing a lower alkoxy group as a substituent on a phenyl ring, a benzimidazolylthio-substituted lower alkyl group, an imidazolylthio-substituted lower alkyl group, a lower alkanoyl group, a cycloalkylthio-substituted lower alkyl group, a cyano-substituted lower alkyl group or a lower trialkyl-substituted ammonium-substituted lower alkyl group, or a salt thereof.

9. The fluorenone derivative according to claim 6, wherein $R^d$, $R^e$, $R^f$ and $R^g$ are a hydrogen atom, a lower alkoxy group, a lower alkyl group, a lower alkenyl group, a lower alkenyloxy group or a halogen atom, or a salt thereof.

10. The fluorenone derivative according to claim 6, wherein $R^d$, $R^e$, $R^f$ and $R^g$ are a group of the formula:

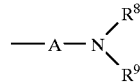

wherein $R^8$ and $R^9$ are the same or different and are a hydrogen atom, a lower alkyl group, a lower alkoxycarbonyl-substituted lower alkyl group, a pyrimidinyl group or pyrazinyl group, and $R^8$ and $R^9$ may bond together with the nitrogen atom to which they are attached to form a 5- or 6-membered saturated heterocycle through a nitrogen or oxygen atom or not, the heterocycle optionally containing a substituent selected from the group consisting of a lower alkyl group and a lower alkoxycarbonyl group; and A is a lower alkylene group, an imidazolyl-substituted lower alkyl group, a lower alkoxy-substituted lower alkyl group, a hydroxyl group-substituted lower alkoxy-lower alkoxy-substituted lower alkyl group or a lower trialkyl-substituted ammonium-substituted lower alkyl group, an imidazolyl-substituted lower alkyl group, a lower alkoxy-substituted lower alkyl group, a pyridylthio-substituted lower alkyl group, a phenylthio-substituted lower alkyl group optionally containing a lower alkoxy group as a substituent on a phenyl ring, a benzimidazolylthio-substituted lower alkyl group, an imidazolylthio-substituted lower alkyl group, a lower alkanoyl group, a cycloalkylthio-substituted lower alkyl group, a cyano-substituted lower alkyl group or a lower trialkyl-substituted ammonium-substituted lower alkyl group, or a salt thereof.

11. The fluorenone derivative according to claim 1, wherein $R^a$ is a lower alkenyl group, or a salt thereof.

12. The fluorenone derivative according to claim 4, wherein r and s are 1 or 2; 1- and/or 3 positions of a fluorenone skeleton are substituted with $R^{1a}$; 6- and/or 8 positions of a fluorenone skeleton are substituted with $R^{2a}$; $R^{1a}$ and $R^{2a}$ are a hydrogen atom, a lower alkyl group or a lower alkenyl group, or a salt thereof.

13. The fluorenone derivative according to claims any one of claims 2 to 4 wherein $R^a$ and $R^h$ are a hydrogen atom or an acetyl group, or a salt thereof.

14. The fluorenone derivative according to claims 2, 3 or 4, wherein $R^a$ and $R^h$ are a lower alkenyl group, or a salt thereof.

15. 1,3,6,8-Tetrapropyl-2,5-dihydroxyfluorenone.

16. 1,3,6,8-Tetrapropyl-2,5-diacetyloxyfluorenone.

17. 1,6-Diallyl-2,5-dihydroxyfluorenone.

18. 1,4-Diallyl-2,5-dihydroxyfluorenone.

19. The fluorenone derivative according to claim 1, wherein $R^a$ is an acetyl group, or a salt thereof.

20. The fluorenone derivative according to claim 2, 3 or 4 wherein $R^a$ and $R^h$ are an acetyl group, or a salt thereof.

21. The fluorenone derivative according to claim 2, 3 or 4, wherein $R^a$ and $R^h$ are a hydrogen atom, or a salt.

22. A method for repairing or protecting central or peripheral nerve degeneration, which comprises using a fluorenone derivative represented by the formula:

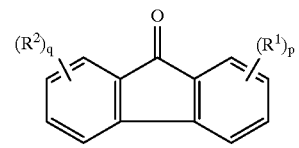

(1)

wherein $R^1$ is a hydrogen atom, a hydroxyl group, a lower alkenyl group, a lower alkyl group, a halogen atom, a lower alkoxy group, a lower alkylthio group, a lower alkanoyloxy group, a lower alkenyloxy group, a group of the formula:

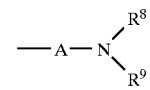

(wherein $R^8$ and $R^9$ are the same or different and are a hydrogen atom, a lower alkyl group, a lower alkoxycarbonyl-substituted lower alkyl group, a pyrimidinyl group or pyrazinyl group, and $R^8$ and $R^9$ may bond together with the nitrogen atom to which they are attached to form a 5- or 6-membered saturated heterocycle through a nitrogen or oxygen atom or not, the heterocycle optionally containing a substituent selected from the group consisting of a lower alkyl group and a lower alkoxycarbonyl group; and A is a lower alkylene group, an imidazolyl-substituted lower alkyl group, a lower alkoxy-substituted lower alkyl group, a hydroxyl group-substituted lower alkoxy-lower alkoxy-substituted lower alkyl group or a lower trialkyl-substituted ammonium-substituted lower alkyl group;

$R^2$ is a hydrogen atom, a hydroxyl group, a lower alkenyl group, a lower alkyl group, a halogen atom, a lower alkoxy group, a lower alkanoyloxy group, a lower alkenyloxy group, a group of the formula:

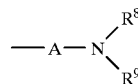

wherein R⁸ and R⁹ are as defined above, an imidazolyl-substituted lower alkyl group, a lower alkoxy-substituted lower alkyl group, a pyridylthio-substituted lower alkyl group, a phenylthio-substituted lower alkyl group optionally containing a lower alkoxy group as a substituent on a phenyl ring, a benzimidazolylthio-substituted lower alkyl group, an imidazolylthio-substituted lower alkyl group, a lower alkanoyl group, a cycloalkylthio-substituted lower alkyl group, a cyano-substituted lower alkyl group or a lower trialkyl-substituted ammonium-substituted lower alkyl group;

p and q are an integer of 1 to 4;

provided that R¹ and R² may be the same or different or a salt thereof.

23. A method for repairing or protecting central or peripheral nerve degeneration according to claim 22 comprising using the compound of claim 1 as an active component.

24. A method for repairing or protecting central or peripheral nerve degeneration according to claim 22 comprising using the compound of claim 2 as an active component.

25. A method for repairing or protecting central or peripheral nerve degeneration according to claim 22 comprising using the compound of claim 3 as an active component.

26. A method for repairing or protecting central or peripheral nerve degeneration according to claim 22 comprising using 1,3,6,8-Tetrapropyl-2,5-dihydroxyfluorenone as an active component.

27. A method for repairing or protecting central or peripheral nerve degeneration according to claim 22 comprising using 1,3,6,8-Tetrapropyl-2,5-diacetyloxyfluorenone as an active component.

28. A method for repairing or protecting central or peripheral nerve degeneration according to claim 22 comprising using 1,6-Diallyl-2,5-dihydroxyfluorenone as an active component.

29. A method for repairing or protecting central or peripheral nerve degeneration according to claim 22 comprising using 1,4,Diallyl-2,5-dihydroxyfluorenone as an active component.

30. A method according to claim 22, wherein the fluorenone derivative is represented by formula (A)

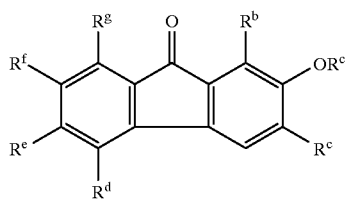

(A)

wherein $R^a$ is a lower alkenyl group or an acetyl group;

$R^b$ and $R^c$ are the same or different and are a hydrogen atom, a lower alkenyl group, a lower alkyl group, a halogen atom, a lower alkoxy group, a lower alkylthio group, a lower alkenyloxy group, a group of the formula:

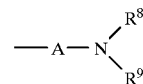

(wherein R⁸ and R⁹ are the same or different and are a hydrogen atom, a lower alkyl group, a lower alkoxycarbonyl-substituted lower alkyl group, a pyrimidinyl group or pyrazinyl group, and R⁸ and R⁹ may bond together with the nitrogen atom to which they are attached to form a 5- or 6-membered saturated heterocycle through a nitrogen or oxygen atom or not, the heterocycle optionally containing a substituent selected from the group consisting of a lower alkyl group and a lower alkoxycarbonyl group; and A is a lower alkylene group), an imidazolyl-substituted lower alkyl group, a lower alkoxy-substituted lower alkyl group, a hydroxyl group-substituted lower alkoxy-lower alkoxy-substituted lower alkyl group or a lower trialkyl-substituted ammonium-substituted lower alkyl group;

$R^d$, $R^e$, $R^f$ and $R^g$ are the same or different and are a hydrogen atom, a lower alkenyl group, a lower alkyl group, a halogen atom, a lower alkoxy group, a lower alkenyloxy group, a group of the formula:

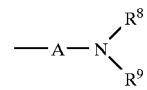

(wherein R⁸ and R⁹ are as above), an imidazolyl-substituted lower alkyl group, a lower alkoxy-substituted lower alkyl group, a pyridylthio-substituted lower alkyl group, a phenylthio-substituted lower alkyl group optionally containing a lower alkoxy group as a substituent on a phenyl ring, a benzimidazolylthio-substituted lower alkyl group, an imidazolylthio-substituted lower alkyl group, a lower alkanoyl group, a cycloalkylthio-substituted lower alkyl group, a cyano-substituted lower alkyl group or a lower trialkyl-substituted ammonium-substituted lower alkyl group;

(i) $R^c$ and $R^g$ must not be methyl groups when $R^a$, $R^b$, $R^d$, $R^e$ and $R^f$ are hydrogen atoms, (ii) $R^g$ must not be a methyl group when $R^b$, $R^c$, $R^e$ and $R^f$ are hydrogen atoms, and $R^a$ an acetyl group, (iii) $R^b$ must not be an allyl group when $R^c$, $R^d$, $R^e$, $R^f$ and $R^g$ are hydrogen atoms, and $R^a$ is an acetyl group, (iv) $R^a$ must not be an allyl group or an acetyl group when $R^b$, $R^d$, $R^e$, $R^f$ and $R^g$ are hydrogen atoms, (v) any one of $R^d$, $R^e$, $R^f$ and $R^g$ must not be a hydrogen atom when $R^b$ and $R^c$ are hydrogen atoms and any one of $R^d$, $R^e$, $R^f$ and $R^g$ is a lower alkenyl group, of a salt thereof.

31. A method according to claim 22, wherein the fluorenone derivative is represented by the formula (C) defined in claim 2.

32. A method according to claim 22, wherein the fluorenone derivative is represented by the formula (C) defined in claim 3.

33. A method according to claim 22, wherein the fluorenone derivative is represented by the formula (C) defined in claim 4.

* * * * *